United States Patent
Henley et al.

(10) Patent No.: US 8,540,687 B2
(45) Date of Patent: Sep. 24, 2013

(54) WOUND TREATMENT APPARATUS

(75) Inventors: Alan Wayne Henley, Summerville, SC (US); Leigh Marie Moses, Summerville, SC (US); Ronald Leslie Sanderson, Charleston, SC (US); John Howard, Charleston, SC (US); James H. Price, Mount Pleasant, SC (US); Russell W. Bessette, Buffalo, NY (US)

(73) Assignee: KCI Licensing, Inc., San Antonio, TX (US)

(*) Notice: Subject to any disclaimer, the term of this patent is extended or adjusted under 35 U.S.C. 154(b) by 0 days.

(21) Appl. No.: 12/860,581

(22) Filed: Aug. 20, 2010

(65) Prior Publication Data

US 2010/0312202 A1    Dec. 9, 2010

Related U.S. Application Data

(62) Division of application No. 11/761,066, filed on Jun. 11, 2007, now Pat. No. 7,794,438, which is a division of application No. 09/743,737, filed as application No. PCT/US99/17877 on Aug. 6, 1999, now Pat. No. 7,276,051, said application No. 11/761,066 is a division of application No. 09/369,113, filed on Aug. 5, 1999, now Pat. No. 6,458,109.

(60) Provisional application No. 60/095,625, filed on Aug. 7, 1998.

(51) Int. Cl.
*A61M 1/00* (2006.01)
*A61M 27/00* (2006.01)
*A61F 13/00* (2006.01)

(52) U.S. Cl.
USPC ............... 604/289; 602/2; 602/41; 602/43; 602/46; 604/290; 604/304; 604/305

(58) Field of Classification Search
USPC ............... 604/289, 290, 294, 304–308
See application file for complete search history.

(56) References Cited

U.S. PATENT DOCUMENTS

| | | | | |
|---|---|---|---|---|
| 765,746 | A | * | 7/1904 | Miner ............... 601/7 |
| 774,529 | A | | 11/1904 | Nieschang ............ 601/14 |
| 1,000,001 | A | | 8/1911 | Holz ............... 601/6 |
| 1,355,846 | A | | 10/1920 | Rannells ............ 604/286 |
| 1,385,346 | A | | 7/1921 | Taylor ............ 604/305 |
| 1,709,520 | A | | 4/1929 | Chandler ............ 292/259 R |
| 1,936,129 | A | | 11/1933 | Fisk ............ 604/313 |

(Continued)

FOREIGN PATENT DOCUMENTS

| AU | 550575 | 8/1982 |
|---|---|---|
| AU | 745271 | 4/1999 |

(Continued)

OTHER PUBLICATIONS

Office Action issued in European Application No. 02 794 392.7, mailed May 3, 2011.

(Continued)

*Primary Examiner* — Kim M Lewis

(57) ABSTRACT

A wound treatment apparatus comprises: a fluid drainage tube configured to be coupled to a fluid drainage passageway of a wound bandage; first and second fluid drainage receptacles coupled to the drainage tube; and first and second valves coupled between the fluid drainage tube and the first and second fluid drainage receptacles, respectively.

18 Claims, 21 Drawing Sheets

(56) References Cited

U.S. PATENT DOCUMENTS

| | | | | |
|---|---|---|---|---|
| 2,078,180 | A | 4/1937 | Kronenberg | 604/28 |
| 2,195,771 | A | 4/1940 | Estler | 604/355 |
| 2,221,758 | A | 11/1940 | Elmquist | 128/888 |
| 2,305,289 | A | 12/1942 | Coburg | 128/132 |
| 2,338,339 | A | 1/1944 | LaMere et al. | 601/7 |
| 2,443,481 | A | 6/1948 | Sene | 128/88 |
| 2,547,758 | A | 4/1951 | Keeling | 128/349 |
| 2,560,915 | A | 7/1951 | Bamberger | 128/350 |
| 2,573,791 | A | 11/1951 | Howells | 602/14 |
| 2,577,945 | A | 12/1951 | Altherton | 602/1 |
| 2,632,443 | A | 3/1953 | Lesher | 128/888 |
| 2,682,873 | A | 7/1954 | Evans et al. | 602/42 |
| 2,910,763 | A | 11/1959 | Lauterbach | 128/72.2 |
| 2,969,057 | A | 1/1961 | Simmons | 128/2 |
| 3,026,874 | A | 3/1962 | Stevens | 604/305 |
| 3,066,672 | A | 12/1962 | Crosby, Jr. et al. | 128/276 |
| 3,315,665 | A | 4/1967 | MacLeod | 601/7 |
| 3,367,332 | A | 2/1968 | Groves | 604/290 |
| 3,382,867 | A | 5/1968 | Reaves | 601/7 |
| 3,430,631 | A | 3/1969 | Abramson | 128/350 |
| 3,492,991 | A | 2/1970 | Dryer | 604/6.09 |
| 3,520,300 | A | 7/1970 | Flower et al. | 604/269 |
| 3,528,416 | A | 9/1970 | Chamberlain | 128/888 |
| 3,568,675 | A | 3/1971 | Harvey | 604/355 |
| 3,585,742 | A | 6/1971 | Tyler | 40/642.02 |
| 3,599,639 | A | 8/1971 | Spotz | 604/119 |
| 3,610,238 | A | 10/1971 | Rich, Jr. | 604/23 |
| 3,623,087 | A | 11/1971 | Gallichotte et al. | 340/509 |
| 3,626,087 | A | 12/1971 | Tomioka | 178/5.4 |
| 3,648,692 | A | 3/1972 | Wheeler | 604/23 |
| 3,682,180 | A | 8/1972 | McFarlane | 128/350 |
| 3,683,894 | A | 8/1972 | Villari | 600/580 |
| 3,721,244 | A | 3/1973 | Elmaleh | 604/128 |
| 3,752,158 | A | 8/1973 | Kariher | 604/133 |
| 3,753,439 | A | 8/1973 | Brugarolas et al. | 128/350 |
| 3,782,377 | A | 1/1974 | Rychlik | 128/888 |
| 3,812,972 | A | 5/1974 | Rosenblum | 210/489 |
| 3,814,095 | A | 6/1974 | Lubens | 604/307 |
| 3,817,145 | A | 6/1974 | Cohen | 84/471 |
| 3,823,720 | A | 7/1974 | Tribble | 128/350 |
| 3,826,254 | A | 7/1974 | Mellor | 128/133 |
| 3,831,588 | A | 8/1974 | Rindner | 600/488 |
| 3,860,008 | A | 1/1975 | Miner et al. | 128/350 |
| 3,874,387 | A | 4/1975 | Barbieri | 602/53 |
| 3,903,882 | A | 9/1975 | Augurt | 602/43 |
| 3,924,624 | A | 12/1975 | Schachet | 128/276 |
| 3,935,863 | A | 2/1976 | Kliger | 604/369 |
| 3,954,105 | A | 5/1976 | Nordby et al. | 604/355 |
| 3,982,546 | A | 9/1976 | Friend | 604/249 |
| 4,004,590 | A | 1/1977 | Muriot | 604/326 |
| 4,013,076 | A | 3/1977 | Puderbaugh et al. | 604/320 |
| RE29,319 | E | 7/1977 | Nordby et al. | 604/355 |
| RE29,321 | E | 7/1977 | Holbrook | 215/309 |
| 4,058,123 | A | 11/1977 | May | 128/278 |
| 4,080,970 | A | 3/1978 | Miller | 604/174 |
| 4,096,853 | A | 6/1978 | Weigand | 128/2 |
| 4,112,947 | A | 9/1978 | Nehring | 604/30 |
| 4,139,004 | A | 2/1979 | Gonzalez, Jr. | 602/14 |
| 4,149,541 | A | 4/1979 | Gammons et al. | 607/104 |
| 4,165,748 | A | 8/1979 | Johnson | 128/348 |
| 4,178,974 | A | 12/1979 | Levin | 141/51 |
| 4,184,510 | A | 1/1980 | Murry et al. | 137/565 |
| 4,191,204 | A | 3/1980 | Nehring | 137/205 |
| 4,219,021 | A | 8/1980 | Fink | 128/214 |
| 4,224,941 | A | 9/1980 | Stivala | 604/23 |
| 4,233,969 | A | 11/1980 | Lock et al. | 128/156 |
| 4,245,630 | A | 1/1981 | Lloyd et al. | 128/155 |
| 4,250,882 | A | 2/1981 | Adair | 604/355 |
| 4,256,109 | A | 3/1981 | Nichols | 128/276 |
| 4,261,363 | A | 4/1981 | Russo | 128/350 |
| 4,275,721 | A | 6/1981 | Olson | 604/180 |
| 4,284,079 | A | 8/1981 | Adair | 128/295 |
| 4,297,995 | A | 11/1981 | Golub | 604/304 |
| 4,333,468 | A | 6/1982 | Geist | 128/348 |
| 4,341,209 | A | 7/1982 | Schaar | 602/58 |
| 4,364,394 | A | 12/1982 | Wilkinson | 604/96 |
| 4,373,519 | A | 2/1983 | Errede et al. | 602/43 |
| 4,382,441 | A | 5/1983 | Svedman | 604/291 |
| 4,392,853 | A | 7/1983 | Muto | 604/171 |
| 4,392,858 | A | 7/1983 | George et al. | 604/187 |
| 4,399,816 | A | 8/1983 | Spangler | 128/888 |
| 4,404,924 | A * | 9/1983 | Goldberg et al. | 116/270 |
| 4,419,097 | A | 12/1983 | Rowland | 604/174 |
| 4,445,897 | A | 5/1984 | Ekbladh et al. | 604/280 |
| 4,457,755 | A | 7/1984 | Wilson | 604/184 |
| 4,460,370 | A | 7/1984 | Allison et al. | 424/448 |
| 4,465,062 | A | 8/1984 | Versaggi et al. | 128/897 |
| 4,465,485 | A | 8/1984 | Kashmer et al. | 604/320 |
| 4,469,092 | A | 9/1984 | Marshall et al. | 601/70 |
| 4,475,909 | A | 10/1984 | Eisenberg | 604/349 |
| 4,480,638 | A | 11/1984 | Schmid | 128/155 |
| 4,508,533 | A | 4/1985 | Abramson | 604/35 |
| 4,525,156 | A | 6/1985 | Benusa et al. | 604/28 |
| 4,525,166 | A | 6/1985 | Leclerc | 604/133 |
| 4,525,374 | A | 6/1985 | Vaillancourt | 427/2 |
| 4,533,352 | A | 8/1985 | Van Beek et al. | 604/317 |
| 4,533,419 | A | 8/1985 | Pieslak et al. | 156/85 |
| 4,540,412 | A | 9/1985 | Van Overloop | 604/291 |
| 4,543,100 | A | 9/1985 | Brodsky | 604/180 |
| 4,548,202 | A | 10/1985 | Duncan | 128/334 |
| 4,551,139 | A | 11/1985 | Plaas et al. | 604/290 |
| 4,553,967 | A | 11/1985 | Ferguson et al. | 604/317 |
| 4,569,348 | A | 2/1986 | Hasslinger | 604/179 |
| 4,569,674 | A | 2/1986 | Phillips et al. | 604/119 |
| 4,573,965 | A | 3/1986 | Russo | 604/30 |
| 4,579,555 | A | 4/1986 | Russo | 604/541 |
| 4,596,564 | A | 6/1986 | Spetzler et al. | 604/281 |
| 4,605,399 | A | 8/1986 | Weston et al. | 604/305 |
| 4,608,041 | A | 8/1986 | Nielsen | 604/23 |
| 4,614,794 | A | 9/1986 | Easton et al. | 530/356 |
| 4,624,656 | A | 11/1986 | Clark et al. | 604/23 |
| 4,633,863 | A | 1/1987 | Filips et al. | 128/846 |
| 4,637,819 | A | 1/1987 | Ouellette et al. | 604/369 |
| 4,640,688 | A | 2/1987 | Hauser | 604/352 |
| 4,641,643 | A | 2/1987 | Greer | 128/888 |
| 4,645,492 | A | 2/1987 | Weeks | 604/174 |
| 4,655,210 | A | 4/1987 | Edenbaum et al. | 602/46 |
| 4,655,754 | A | 4/1987 | Richmond et al. | 604/323 |
| 4,661,093 | A | 4/1987 | Beck et al. | 604/543 |
| 4,664,652 | A | 5/1987 | Weilbacher | 604/133 |
| 4,664,662 | A | 5/1987 | Webster | 602/47 |
| 4,667,666 | A | 5/1987 | Fryslie | 128/888 |
| 4,679,590 | A | 7/1987 | Hergenroeer | 137/602 |
| 4,704,102 | A | 11/1987 | Guthery | 604/28 |
| 4,710,165 | A | 12/1987 | McNeil et al. | 604/67 |
| 4,713,051 | A | 12/1987 | Steppe et al. | 604/30 |
| 4,717,332 | A | 1/1988 | Edens | 431/8 |
| 4,717,379 | A | 1/1988 | Ekholmer | 604/43 |
| 4,717,382 | A | 1/1988 | Clemens et al. | 604/122 |
| 4,728,323 | A | 3/1988 | Matson | 604/304 |
| 4,733,659 | A | 3/1988 | Edenbaum et al. | 602/54 |
| 4,735,606 | A | 4/1988 | Davison | 604/28 |
| 4,735,610 | A | 4/1988 | Akkas et al. | 604/119 |
| 4,737,148 | A | 4/1988 | Blake | 604/126 |
| 4,740,202 | A | 4/1988 | Stacey et al. | 604/119 |
| 4,743,232 | A | 5/1988 | Kruger | 604/180 |
| 4,747,166 | A | 5/1988 | Kuntz | 4/144.1 |
| 4,758,220 | A | 7/1988 | Sundblom et al. | 604/65 |
| 4,759,354 | A | 7/1988 | Quarfoot | 602/50 |
| 4,765,316 | A | 8/1988 | Marshall | 601/70 |
| 4,778,446 | A | 10/1988 | Jensen | 604/27 |
| 4,778,456 | A | 10/1988 | Lokken | 604/290 |
| 4,787,888 | A | 11/1988 | Fox | 604/20 |
| 4,795,428 | A * | 1/1989 | Hwang | 604/73 |
| 4,798,578 | A | 1/1989 | Ranford | 604/6.09 |
| 4,820,265 | A | 4/1989 | DeSatnick et al. | 604/30 |
| 4,820,284 | A | 4/1989 | Hauri | 604/318 |
| 4,826,494 | A | 5/1989 | Richmond et al. | 604/323 |
| 4,826,949 | A | 5/1989 | Stanko | 528/272 |
| 4,834,110 | A | 5/1989 | Richard | 600/573 |
| 4,838,883 | A | 6/1989 | Matsuura | 604/349 |
| 4,840,187 | A | 6/1989 | Brazier | 128/844 |
| 4,841,962 | A | 6/1989 | Berg et al. | 128/156 |
| 4,850,350 | A | 7/1989 | Jackson | 128/207.16 |

| Patent No. | Date | Inventor | Class |
|---|---|---|---|
| 4,863,449 A | 9/1989 | Therriault et al. | 604/352 |
| 4,872,450 A | 10/1989 | Austad | 602/48 |
| 4,878,901 A | 11/1989 | Sachse | 604/174 |
| 4,890,608 A | 1/1990 | Steer | 602/57 |
| 4,897,081 A | 1/1990 | Poirer et al. | 604/175 |
| 4,900,302 A | 2/1990 | Newton | 604/30 |
| 4,902,508 A | 2/1990 | Badylak et al. | 424/95 |
| 4,906,233 A | 3/1990 | Moriuchi et al. | 604/174 |
| 4,906,240 A | 3/1990 | Reed et al. | 604/307 |
| 4,915,694 A | 4/1990 | Yamamoto et al. | 604/180 |
| 4,917,112 A | 4/1990 | Kalt | 602/58 |
| 4,919,654 A | 4/1990 | Kalt | 604/180 |
| 4,921,492 A | 5/1990 | Schultz et al. | 604/315 |
| 4,930,997 A | 6/1990 | Bennett | 471/410 |
| 4,941,882 A | 7/1990 | Ward et al. | 604/180 |
| 4,950,230 A | 8/1990 | Kendell | 604/28 |
| 4,953,565 A | 9/1990 | Tachibana et al. | 607/152 |
| 4,956,178 A | 9/1990 | Badylak et al. | 424/551 |
| 4,957,492 A | 9/1990 | McVay | 604/319 |
| 4,962,761 A | 10/1990 | Golden | 607/104 |
| 4,969,880 A | 11/1990 | Zamierowski | 604/305 |
| 4,969,881 A | 11/1990 | Viesturs | 604/305 |
| 4,970,298 A | 11/1990 | Silver et al. | 530/356 |
| 4,985,019 A | 1/1991 | Michelson | 604/180 |
| 4,988,336 A | 1/1991 | Kohn | 604/67 |
| 4,990,144 A | 2/1991 | Blott | 604/304 |
| 4,991,574 A | 2/1991 | Pocknell | 602/48 |
| 4,994,022 A | 2/1991 | Steffler et al. | 604/7 |
| 4,997,425 A | 3/1991 | Shioya et al. | 604/304 |
| 5,000,172 A | 3/1991 | Ward | 128/155 |
| 5,000,741 A | 3/1991 | Kalt | 604/180 |
| 5,002,528 A | 3/1991 | Palestrant | 604/28 |
| 5,002,529 A | 3/1991 | Cunningham | 604/73 |
| 5,003,971 A | 4/1991 | Buckley | 602/54 |
| 5,014,389 A | 5/1991 | Ogilvie et al. | 15/353 |
| 5,034,003 A | 7/1991 | Denance | 604/117 |
| 5,034,006 A | 7/1991 | Hosoda et al. | 604/317 |
| 5,035,865 A | 7/1991 | Inaba et al. | 422/99 |
| 5,037,397 A | 8/1991 | Kalt et al. | 604/174 |
| 5,042,978 A | 8/1991 | Quenin et al. | 604/317 |
| 5,045,777 A | 9/1991 | Itagaki | 324/76.12 |
| 5,060,662 A | 10/1991 | Farnswoth, III | 128/888 |
| 5,069,907 A | 12/1991 | Mixon et al. | 424/445 |
| 5,071,409 A | 12/1991 | Rosenberg | 604/119 |
| 5,073,172 A | 12/1991 | Fell | 604/319 |
| 5,080,650 A | 1/1992 | Hirsch et al. | 604/104 |
| 5,086,170 A | 2/1992 | Luheshi et al. | 540/303 |
| 5,086,763 A | 2/1992 | Hathman | 602/42 |
| 5,086,764 A | 2/1992 | Gilman | 602/42 |
| 5,092,858 A | 3/1992 | Benson et al. | 604/319 |
| 5,100,395 A | 3/1992 | Rosenberg | 604/284 |
| 5,100,396 A | 3/1992 | Zamierowski | 604/305 |
| 5,101,808 A | 4/1992 | Kobayashi et al. | 601/44 |
| 5,106,362 A | 4/1992 | Gilman | 602/47 |
| 5,106,629 A | 4/1992 | Cartmell et al. | 424/445 |
| 5,108,364 A | 4/1992 | Takezawa et al. | 604/43 |
| 5,134,994 A | 8/1992 | Say | 128/200.24 |
| 5,135,518 A | 8/1992 | Vera | 604/291 |
| 5,146,925 A | 9/1992 | Snow | 600/435 |
| 5,147,338 A | 9/1992 | Lang et al. | 604/304 |
| 5,149,331 A | 9/1992 | Ferdman et al. | 604/290 |
| 5,152,757 A | 10/1992 | Eriksson | 604/305 |
| 5,160,322 A | 11/1992 | Scheremet et al. | 604/122 |
| 5,167,613 A | 12/1992 | Karami et al. | 602/42 |
| 5,167,622 A | 12/1992 | Muto | 604/35 |
| 5,170,781 A | 12/1992 | Loomis | 128/118.1 |
| 5,176,502 A | 1/1993 | Sanderson et al. | 417/18 |
| 5,176,663 A | 1/1993 | Svedman et al. | 604/305 |
| 5,176,667 A | 1/1993 | DeBring | 604/356 |
| 5,181,908 A | 1/1993 | Bell | 604/24 |
| 5,189,609 A | 2/1993 | Tivig et al. | 600/300 |
| 5,197,948 A | 3/1993 | Ghodsian | 604/30 |
| 5,215,522 A | 6/1993 | Page et al. | 604/33 |
| 5,215,539 A | 6/1993 | Schoolman | 604/541 |
| 5,224,929 A | 7/1993 | Remiszewski | 604/30 |
| 5,228,431 A | 7/1993 | Giarretto | 601/9 |
| 5,230,350 A | 7/1993 | Fentress | 128/846 |
| 5,232,453 A | 8/1993 | Plass et al. | 604/180 |
| 5,238,654 A | 8/1993 | Nohl et al. | 422/100 |
| 5,249,121 A | 9/1993 | Baum et al. | 606/1 |
| 5,256,418 A | 10/1993 | Kemp et al. | 424/423 |
| 5,261,893 A | 11/1993 | Zamierowski | 604/180 |
| 5,263,922 A | 11/1993 | Sova et al. | 602/59 |
| 5,265,605 A | 11/1993 | Afflerbach | 600/300 |
| 5,275,826 A | 1/1994 | Badylak et al. | 424/551 |
| 5,278,100 A | 1/1994 | Doan et al. | 437/200 |
| 5,279,550 A | 1/1994 | Habib et al. | 604/38 |
| 5,281,422 A | 1/1994 | Badylak et al. | 424/551 |
| 5,291,887 A | 3/1994 | Stanley et al. | 600/529 |
| 5,298,015 A | 3/1994 | Komatsuzaki et al. | 602/46 |
| 5,306,298 A | 4/1994 | Godley, III et al. | 623/9 |
| 5,314,409 A | 5/1994 | Sarosiek et al. | 604/101 |
| 5,330,452 A | 7/1994 | Zook | 604/307 |
| 5,335,651 A | 8/1994 | Foster et al. | 128/202.13 |
| 5,338,293 A | 8/1994 | Jeppsson et al. | 604/29 |
| 5,342,293 A | 8/1994 | Zanger | 604/22 |
| 5,342,301 A | 8/1994 | Saab | 604/96 |
| 5,342,376 A | 8/1994 | Ruff | 606/151 |
| 5,344,415 A | 9/1994 | DeBusk et al. | 604/304 |
| 5,349,965 A | 9/1994 | McCarver | 128/846 |
| 5,352,463 A | 10/1994 | Badylak et al. | 424/551 |
| 5,358,494 A | 10/1994 | Svedman | 604/313 |
| 5,370,610 A | 12/1994 | Reynolds | 604/43 |
| 5,372,821 A | 12/1994 | Badylak et al. | 424/551 |
| 5,374,254 A | 12/1994 | Burma | 604/175 |
| 5,376,252 A | 12/1994 | Eckstrom et al. | 204/603 |
| 5,380,280 A | 1/1995 | Peterson | 604/65 |
| 5,395,315 A | 3/1995 | Griep | 604/35 |
| 5,409,013 A | 4/1995 | Clement | 128/753 |
| 5,413,788 A | 5/1995 | Edwards et al. | 424/409 |
| 5,419,768 A | 5/1995 | Kayser | 604/119 |
| 5,431,622 A | 7/1995 | Pyrozyk et al. | 602/2 |
| 5,437,622 A | 8/1995 | Carion | 602/57 |
| 5,437,651 A | 8/1995 | Todd et al. | 604/313 |
| 5,439,452 A | 8/1995 | McCarty | 604/248 |
| 5,445,604 A | 8/1995 | Lang | 602/47 |
| 5,445,833 A | 8/1995 | Badylak et al. | 424/551 |
| 5,447,505 A | 9/1995 | Valentine et al. | 604/304 |
| 5,449,383 A | 9/1995 | Chatelier et al. | 623/1 |
| 5,451,215 A | 9/1995 | Wolter | 604/265 |
| 5,451,373 A | 9/1995 | Lewis et al. | 422/82.13 |
| 5,478,333 A | 12/1995 | Asherman, Jr. | 604/304 |
| 5,484,420 A | 1/1996 | Russo | 604/178 |
| 5,484,427 A | 1/1996 | Gibbons | 604/313 |
| 5,484,428 A | 1/1996 | Drainville et al. | 604/319 |
| 5,487,889 A | 1/1996 | Eckert et al. | 424/93.1 |
| 5,516,533 A | 5/1996 | Badylak et al. | 424/551 |
| 5,520,652 A | 5/1996 | Peterson | 604/119 |
| 5,527,293 A | 6/1996 | Zamierowski | 604/176 |
| 5,531,670 A | 7/1996 | Westby et al. | 602/41 |
| 5,533,981 A | 7/1996 | Mandro et al. | 604/208 |
| 5,534,346 A | 7/1996 | Robinson | 428/343 |
| 5,540,668 A | 7/1996 | Wilson et al. | 604/248 |
| 5,542,918 A | 8/1996 | Atkinson | 604/27 |
| 5,549,584 A | 8/1996 | Gross | 604/313 |
| 5,554,389 A | 9/1996 | Badylak et al. | 424/558 |
| 5,556,375 A | 9/1996 | Ewall | 602/58 |
| 5,558,639 A | 9/1996 | Gangemi et al. | 604/67 |
| 5,573,784 A | 11/1996 | Badylak et al. | 424/551 |
| 5,578,022 A | 11/1996 | Scherson et al. | 604/304 |
| 5,578,662 A | 11/1996 | Bennett et al. | 524/54 |
| 5,607,388 A | 3/1997 | Ewall | 602/58 |
| 5,607,683 A | 3/1997 | Capelli | 424/405 |
| 5,616,338 A | 4/1997 | Fox et al. | 424/423 |
| 5,621,035 A | 4/1997 | Lyles et al. | 524/404 |
| 5,624,417 A * | 4/1997 | Cook et al. | 604/319 |
| 5,624,418 A | 4/1997 | Shepard | 604/319 |
| 5,628,735 A | 5/1997 | Skow | 604/317 |
| 5,629,186 A | 5/1997 | Yasukawa et al. | 435/177 |
| 5,631,011 A | 5/1997 | Wadström | 424/400 |
| 5,635,201 A | 6/1997 | Fabo | 424/443 |
| 5,636,643 A | 6/1997 | Argenta et al. | 128/897 |
| 5,641,518 A | 6/1997 | Badylak et al. | 424/551 |
| 5,645,081 A | 7/1997 | Argenta et al. | 128/897 |
| 5,645,860 A | 7/1997 | Knapp et al. | 424/551 |
| 5,655,258 A | 8/1997 | Heintz | 15/415.1 |
| 5,656,027 A | 8/1997 | Ellingboe | 604/541 |
| 5,662,598 A | 9/1997 | Tobin | 602/41 |

| | | | |
|---|---|---|---|
| 5,662,624 A | 9/1997 | Sundstrom et al. ............ 604/291 |
| 5,662,625 A | 9/1997 | Westwood ...................... 604/305 |
| 5,669,892 A | 9/1997 | Keogh et al. ................... 604/320 |
| 5,672,151 A | 9/1997 | Calderon-Garcidueñas ... 602/21 |
| 5,672,152 A | 9/1997 | Mason et al. .................... 602/26 |
| 5,674,193 A | 10/1997 | Hayes .............................. 604/28 |
| 5,678,564 A | 10/1997 | Lawrence et al. .............. 600/574 |
| 5,681,290 A | 10/1997 | Alexander ...................... 604/180 |
| 5,690,815 A | 11/1997 | Krasnoff et al. ................ 210/97 |
| 5,695,998 A | 12/1997 | Badylak et al. ................. 435/391 |
| 5,697,920 A | 12/1997 | Gibbons .......................... 604/289 |
| 5,711,969 A | 1/1998 | Patel et al. ...................... 424/551 |
| 5,718,955 A | 2/1998 | McGuire et al. ............... 428/35.7 |
| 5,735,833 A | 4/1998 | Olson .............................. 604/289 |
| 5,738,656 A | 4/1998 | Wagner ........................... 604/119 |
| 5,741,237 A | 4/1998 | Walker ............................ 604/317 |
| 5,749,842 A | 5/1998 | Cheong et al. .................. 602/41 |
| 5,753,267 A | 5/1998 | Badylak et al. ................. 424/551 |
| 5,755,791 A | 5/1998 | Whitson et al. ................. 623/15 |
| 5,759,570 A | 6/1998 | Arnold ............................ 424/443 |
| 5,762,640 A | 6/1998 | Kajiwara et al. ............... 604/313 |
| 5,762,966 A | 6/1998 | Knapp et al. .................... 424/551 |
| 5,780,281 A | 7/1998 | Yasukawa et al. .............. 435/176 |
| 5,782,871 A | 7/1998 | Fujiwara et al. ................ 604/313 |
| 5,795,584 A | 8/1998 | Totakura et al. ................ 424/426 |
| 5,800,383 A | 9/1998 | Chandler et al. ............... 604/35 |
| 5,817,145 A | 10/1998 | Augustine et al. .............. 607/96 |
| 5,827,246 A | 10/1998 | Bowen ............................ 604/313 |
| 5,827,296 A | 10/1998 | Morris et al. ................... 606/129 |
| 5,855,619 A | 1/1999 | Caplan et al. ................... 623/11 |
| 5,866,414 A | 2/1999 | Badylak et al. ................. 435/325 |
| 5,881,723 A | 3/1999 | Wallace et al. ............ 128/204.21 |
| 5,891,111 A | 4/1999 | Ismael ............................. 604/280 |
| 5,902,874 A | 5/1999 | Roby et al. ...................... 528/310 |
| 5,902,875 A | 5/1999 | Roby et al. ...................... 528/310 |
| 5,911,222 A | 6/1999 | Lawrence et al. .............. 600/574 |
| 5,914,387 A | 6/1999 | Roby et al. ...................... 528/310 |
| 5,919,476 A | 7/1999 | Fischer et al. .................. 424/443 |
| 5,921,972 A | 7/1999 | Skow ............................... 604/313 |
| 5,928,174 A | 7/1999 | Gibbins ........................... 602/41 |
| 5,931,304 A | 8/1999 | Hammond ....................... 206/570 |
| 5,941,859 A | 8/1999 | Lerman ........................... 604/289 |
| 5,942,496 A | 8/1999 | Bonadio et al. ................. 514/44 |
| 5,947,914 A | 9/1999 | Augustine ....................... 602/2 |
| 5,951,295 A | 9/1999 | Lyles et al. ..................... 433/228.1 |
| 5,954,680 A | 9/1999 | Augustine ....................... 602/42 |
| 5,961,480 A | 10/1999 | Augustine ....................... 602/41 |
| 5,962,427 A | 10/1999 | Goldstein et al. ............... 514/44 |
| 5,964,721 A | 10/1999 | Augustine ....................... 602/2 |
| 5,964,723 A | 10/1999 | Augustine ....................... 602/42 |
| 5,986,163 A | 11/1999 | Augustine ....................... 602/42 |
| 5,997,568 A | 12/1999 | Liu .................................. 606/228 |
| 6,010,527 A | 1/2000 | Augustine et al. .............. 607/96 |
| 6,013,048 A | 1/2000 | Podany et al. ................... 604/22 |
| 6,017,493 A | 1/2000 | Cambron et al. ............... 422/44 |
| 6,039,724 A | 3/2000 | Seifert et al. .................... 604/533 |
| 6,045,518 A | 4/2000 | Augustine ....................... 602/2 |
| 6,045,541 A | 4/2000 | Matsumoto et al. ............ 604/313 |
| 6,051,747 A | 4/2000 | Lindqvist et al. ............... 602/46 |
| 6,056,730 A | 5/2000 | Greter ............................. 604/319 |
| 6,071,254 A | 6/2000 | Augustine ....................... 602/2 |
| 6,071,267 A | 6/2000 | Zamierowski ................... 604/313 |
| 6,071,304 A | 6/2000 | Augustine et al. .............. 607/96 |
| 6,080,189 A | 6/2000 | Augustine et al. .............. 607/96 |
| 6,080,243 A | 6/2000 | Insley et al. ..................... 134/21 |
| 6,093,160 A | 7/2000 | Augustine et al. .............. 602/2 |
| 6,093,230 A | 7/2000 | Johnson et al. ................. 55/482 |
| 6,095,992 A | 8/2000 | Augustine et al. .............. 602/2 |
| 6,099,567 A | 8/2000 | Badylak et al. ................. 623/13 |
| 6,110,197 A | 8/2000 | Augustine ....................... 607/108 |
| 6,113,561 A | 9/2000 | Augustine ....................... 602/2 |
| 6,117,111 A | 9/2000 | Fleischmann ................... 604/313 |
| 6,135,116 A | 10/2000 | Vogel et al. ..................... 128/898 |
| 6,142,982 A | 11/2000 | Hunt et al. ...................... 604/313 |
| 6,143,945 A | 11/2000 | Augustine et al. .............. 602/41 |
| 6,149,614 A | 11/2000 | Dunshee et al. ................ 602/57 |
| 6,171,344 B1 | 1/2001 | Atala ............................... 623/23.64 |
| 6,174,306 B1 | 1/2001 | Fleischmann ................... 604/543 |
| 6,203,563 B1 | 3/2001 | Fernandez ....................... 606/215 |
| 6,206,931 B1 | 3/2001 | Cook et al. ...................... 623/23.75 |
| 6,207,875 B1 | 3/2001 | Lindqvist et al. ............... 602/46 |
| 6,213,965 B1 | 4/2001 | Augustine et al. .............. 602/2 |
| 6,213,966 B1 | 4/2001 | Augustine ....................... 602/2 |
| 6,217,535 B1 | 4/2001 | Augustine ....................... 602/2 |
| 6,235,009 B1 | 5/2001 | Skow ............................... 604/317 |
| 6,235,047 B1 | 5/2001 | Augustine et al. .............. 607/96 |
| 6,241,697 B1 | 6/2001 | Augustine ....................... 602/2 |
| 6,241,698 B1 | 6/2001 | Augustine ....................... 602/2 |
| 6,241,747 B1 | 6/2001 | Ruff ................................ 606/216 |
| 6,244,311 B1 | 6/2001 | Hand et al. ...................... 141/375 |
| 6,248,084 B1 | 6/2001 | Augustine et al. .............. 602/2 |
| 6,254,557 B1 | 7/2001 | Augustine et al. .............. 602/2 |
| 6,254,580 B1 | 7/2001 | Svedman ......................... 604/313 |
| 6,259,067 B1 | 7/2001 | Faries, Jr. et al. ............... 219/428 |
| 6,264,622 B1 | 7/2001 | Augustine ....................... 602/2 |
| 6,264,979 B1 | 7/2001 | Svedman ......................... 424/449 |
| 6,267,740 B1 | 7/2001 | Augustine ....................... 602/2 |
| 6,283,931 B1 | 9/2001 | Augustine ....................... 602/2 |
| 6,284,941 B1 | 9/2001 | Cox et al. ........................ 602/48 |
| 6,287,316 B1 | 9/2001 | Agarwal et al. ................. 606/151 |
| 6,290,685 B1 | 9/2001 | Insley et al. ..................... 604/317 |
| 6,293,917 B1 | 9/2001 | Augustine et al. .............. 602/2 |
| 6,325,798 B1 | 12/2001 | Edwards et al. ................ 606/41 |
| 6,345,623 B1 | 2/2002 | Heaton et al. ................... 128/897 |
| 6,364,853 B1 | 4/2002 | French et al. ................... 604/35 |
| 6,394,142 B1 | 5/2002 | Woelfel et al. .................. 138/115 |
| 6,398,767 B1* | 6/2002 | Fleischmann ................... 604/313 |
| 6,410,427 B1 | 6/2002 | Hu .................................. 438/655 |
| 6,440,427 B1 | 8/2002 | Wadström ....................... 424/400 |
| 6,458,109 B1 | 10/2002 | Henley et al. ................... 604/304 |
| 6,471,685 B1 | 10/2002 | Johnson .......................... 604/890.1 |
| 6,472,581 B1 | 10/2002 | Muramatsu et al. ............ 602/41 |
| 6,488,643 B1 | 12/2002 | Turney et al. ................... 602/13 |
| 6,491,682 B2 | 12/2002 | Paderni ........................... 604/541 |
| 6,491,693 B1 | 12/2002 | Lytinas ........................... 606/53 |
| 6,493,568 B1 | 12/2002 | Bell et al. ........................ 600/323 |
| 6,500,112 B1 | 12/2002 | Khouri ............................ 600/38 |
| 6,520,982 B1 | 2/2003 | Boynton et al. ................. 607/104 |
| 6,553,998 B2 | 4/2003 | Heaton et al. ................... 128/897 |
| 6,557,704 B1 | 5/2003 | Randolph ........................ 206/363 |
| 6,559,773 B1 | 5/2003 | Berry .............................. 340/815.4 |
| 6,599,277 B2 | 7/2003 | Neubert ........................... 604/317 |
| 6,626,891 B2 | 9/2003 | Ohmstede ....................... 604/543 |
| 6,638,270 B2 | 10/2003 | Johnson .......................... 604/890.1 |
| 6,648,862 B2 | 11/2003 | Watson ........................... 604/319 |
| 6,663,349 B1 | 12/2003 | Discenzo et al. ............... 417/44.1 |
| 6,685,681 B2 | 2/2004 | Lockwood et al. ............. 604/305 |
| 6,691,047 B1 | 2/2004 | Fredericks ....................... 702/47 |
| 6,695,823 B1 | 2/2004 | Lina et al. ....................... 604/304 |
| 6,695,824 B2 | 2/2004 | Howard et al. ................. 604/305 |
| 6,719,779 B2 | 4/2004 | Daoud ............................. 607/105 |
| 6,749,592 B2 | 6/2004 | Lord ................................ 604/319 |
| 6,752,794 B2 | 6/2004 | Lockwood et al. ............. 604/313 |
| 6,755,807 B2 | 6/2004 | Risk, Jr. et al. ................. 604/319 |
| 6,764,462 B2 | 7/2004 | Risk, Jr. et al. ................. 604/67 |
| 6,767,334 B1 | 7/2004 | Randolph ........................ 604/35 |
| 6,794,554 B2 | 9/2004 | Sessions et al. ................ 602/46 |
| 6,800,074 B2 | 10/2004 | Henley et al. ................... 604/319 |
| 6,814,079 B2 | 11/2004 | Heaton et al. ................... 128/897 |
| 6,824,533 B2 | 11/2004 | Risk, Jr. et al. ................. 604/319 |
| 6,855,135 B2 | 2/2005 | Lockwood et al. ............. 604/313 |
| 6,856,821 B2 | 2/2005 | Johnson .......................... 600/345 |
| 6,936,037 B2 | 8/2005 | Bubb et al. ...................... 604/327 |
| 6,951,553 B2 | 10/2005 | Bubb et al. ...................... 604/327 |
| 6,966,889 B2 | 11/2005 | Saab ................................ 604/96.01 |
| 6,979,324 B2 | 12/2005 | Bybordi et al. ................. 604/313 |
| 6,994,702 B1 | 2/2006 | Johnson .......................... 606/9 |
| 6,994,708 B2 | 2/2006 | Manzo ............................ 606/45 |
| 7,004,915 B2 | 2/2006 | Boynton et al. ................. 601/6 |
| 7,022,113 B2 | 4/2006 | Lockwood et al. ............. 604/313 |
| 7,070,584 B2 | 7/2006 | Johnson et al. ................. 604/313 |
| 7,077,832 B2 | 7/2006 | Fleischmann ................... 604/304 |
| 7,108,683 B2 | 9/2006 | Zamierowski ................... 604/304 |
| 7,117,869 B2 | 10/2006 | Heaton et al. ................... 128/897 |
| 7,128,735 B2 | 10/2006 | Weston ............................ 604/543 |
| 7,144,390 B1 | 12/2006 | Hannigan et al. ............... 604/313 |
| 7,195,624 B2 | 3/2007 | Lockwood et al. ............. 604/543 |
| 7,216,651 B2 | 5/2007 | Argenta et al. .................. 128/897 |

| | | | |
|---|---|---|---|
| 7,245,291 B2 | 7/2007 | Sharif et al. ............... 345/172 |
| 7,273,054 B2 | 9/2007 | Heaton et al. ............... 128/897 |
| 7,276,051 B1 | 10/2007 | Henley et al. ............... 604/304 |
| 7,338,482 B2 | 3/2008 | Lockwood et al. .......... 604/543 |
| 7,351,250 B2 | 4/2008 | Zamierowski ............... 606/215 |
| 7,381,211 B2 | 6/2008 | Zamierowski ............... 606/215 |
| 7,381,859 B2 | 6/2008 | Hunt ............................. 602/46 |
| 7,410,495 B2 | 8/2008 | Zamierowski ............... 606/216 |
| 7,413,570 B2 | 8/2008 | Zamierowski ............... 606/215 |
| 7,413,571 B2 | 8/2008 | Zamierowski ............... 606/215 |
| 7,422,576 B2 | 9/2008 | Boynton et al. ............. 604/291 |
| 7,524,286 B2 | 4/2009 | Johnson ........................ 600/309 |
| 7,534,927 B2 | 5/2009 | Lockwood et al. .......... 602/46 |
| 7,618,382 B2 | 11/2009 | Vogel et al. .................. 601/7 |
| 2001/0029956 A1 | 10/2001 | Argenta et al. ............... 128/897 |
| 2001/0034499 A1 | 10/2001 | Sessions et al. ............. 128/897 |
| 2001/0043943 A1 | 11/2001 | Coffey .......................... 424/447 |
| 2001/0052681 A1 | 12/2001 | Deavila ........................ 280/47.19 |
| 2002/0065494 A1 | 5/2002 | Lockwood et al. .......... 604/313 |
| 2002/0077661 A1 | 6/2002 | Saadat .......................... 606/221 |
| 2002/0082567 A1 | 6/2002 | Lockwood et al. .......... 604/313 |
| 2002/0082688 A1 | 6/2002 | Sander et al. ................ 623/2.13 |
| 2002/0085952 A1 | 7/2002 | Ellingboe et al. ............ 422/45 |
| 2002/0115951 A1 | 8/2002 | Norstrem et al. ............ 602/27 |
| 2002/0115952 A1 | 8/2002 | Johnson et al. .............. 602/41 |
| 2002/0120185 A1 | 8/2002 | Johnson ........................ 600/345 |
| 2002/0143286 A1 | 10/2002 | Tumey .......................... 604/11 |
| 2002/0161317 A1 | 10/2002 | Risk et al. .................... 602/2 |
| 2002/0161346 A1 | 10/2002 | Lockwood et al. .......... 604/315 |
| 2002/0183702 A1 | 12/2002 | Henley et al. ................ 604/305 |
| 2002/0193723 A1 | 12/2002 | Batdorf et al. ............... 602/48 |
| 2003/0032951 A1 | 2/2003 | Rittman et al. ............... 606/34 |
| 2003/0077311 A1 | 4/2003 | Vyakarnam et al. ......... 435/41 |
| 2003/0093041 A1 | 5/2003 | Risk, Jr. et al. ............. 604/304 |
| 2003/0143352 A1 | 7/2003 | Yang et al. ................... 428/36.9 |
| 2003/0208149 A1 | 11/2003 | Coffey .......................... 602/48 |
| 2003/0219469 A1 | 11/2003 | Johnson et al. .............. 424/445 |
| 2003/0225441 A1 | 12/2003 | Boynton et al. ............. 607/104 |
| 2004/0030304 A1 | 2/2004 | Hunt et al. ................... 604/304 |
| 2004/0039415 A1 | 2/2004 | Zamierowski ............... 606/216 |
| 2004/0064111 A1 | 4/2004 | Lockwood et al. .......... 604/305 |
| 2004/0167482 A1 | 8/2004 | Watson ......................... 604/317 |
| 2004/0225208 A1 | 11/2004 | Johnson ........................ 600/364 |
| 2004/0243073 A1 | 12/2004 | Lockwood et al. .......... 604/313 |
| 2004/0249353 A1 | 12/2004 | Risks et al. .................. 604/315 |
| 2004/0260230 A1 | 12/2004 | Randolph ...................... 604/28 |
| 2005/0004534 A1 | 1/2005 | Lockwood et al. .......... 604/304 |
| 2005/0010153 A1 | 1/2005 | Lockwood et al. .......... 602/41 |
| 2005/0033197 A1 | 2/2005 | Cottler ......................... 600/573 |
| 2005/0065484 A1 | 3/2005 | Watson ......................... 604/289 |
| 2005/0070858 A1 | 3/2005 | Lockwood et al. .......... 604/319 |
| 2005/0085795 A1 | 4/2005 | Lockwood et al. .......... 604/543 |
| 2005/0090787 A1 | 4/2005 | Risk et al. .................... 604/315 |
| 2005/0131327 A1 | 6/2005 | Lockwood et al. .......... 602/41 |
| 2005/0177190 A1 | 8/2005 | Zamierowski ............... 606/215 |
| 2005/0182445 A1 | 8/2005 | Zamierowski ............... 606/213 |
| 2005/0182446 A1 | 8/2005 | DeSantis ....................... 606/222 |
| 2005/0234485 A1 | 10/2005 | Seegert et al. ............... 606/172 |
| 2005/0234510 A1 | 10/2005 | Zamierowski ............... 606/215 |
| 2005/0240220 A1 | 10/2005 | Zamierowski ............... 606/215 |
| 2005/0283105 A1 | 12/2005 | Heaton et al. ............... 128/897 |
| 2006/0015087 A1 | 1/2006 | Risk et al. .................... 604/541 |
| 2006/0029650 A1 | 2/2006 | Coffey .......................... 424/443 |
| 2006/0029675 A1 | 2/2006 | Ginther ........................ 424/486 |
| 2006/0041247 A1 | 2/2006 | Petrosenko et al. ......... 604/543 |
| 2006/0079852 A1 | 4/2006 | Bubb ............................ 604/317 |
| 2006/0129137 A1 | 6/2006 | Lockwood et al. .......... 604/543 |
| 2006/0149170 A1 | 7/2006 | Boynton et al. ............. 601/6 |
| 2006/0149171 A1 | 7/2006 | Vogel et al. .................. 601/11 |
| 2006/0173253 A1 | 8/2006 | Ganapathy et al. ......... 600/310 |
| 2006/0189910 A1 | 8/2006 | Johnson et al. .............. 602/42 |
| 2006/0213527 A1 | 9/2006 | Argenta et al. ............... 128/897 |
| 2007/0005028 A1 | 1/2007 | Risk et al. .................... 604/315 |
| 2007/0014837 A1 | 1/2007 | Johnson et al. .............. 424/443 |
| 2007/0021697 A1 | 1/2007 | Ginther et al. ............... 602/1 |
| 2007/0021698 A1 | 1/2007 | Fleischmann ................ 602/2 |
| 2007/0032778 A1 | 2/2007 | Heaton et al. ............... 604/540 |
| 2007/0038172 A1 | 2/2007 | Zamierowski ............... 604/20 |
| 2007/0156104 A1 | 7/2007 | Lockwood et al. .......... 604/305 |
| 2007/0233022 A1 | 10/2007 | Henley et al. ................ 604/304 |
| 2009/0082740 A1 | 3/2009 | Lockwood et al. .......... 602/41 |
| 2010/0063483 A1 | 3/2010 | Adahan ........................ 604/543 |

FOREIGN PATENT DOCUMENTS

| | | |
|---|---|---|
| AU | 755496 | 2/2002 |
| CA | 1127488 | 7/1982 |
| CA | 2005436 | 6/1990 |
| CA | 2303085 | 3/1999 |
| DE | 0372727 | 3/1923 |
| DE | 2640413 | 3/1978 |
| DE | 2809828 | 9/1978 |
| DE | 3102674 | 9/1982 |
| DE | 3539533 | 5/1987 |
| DE | 4012232 | 10/1991 |
| DE | 4111122 | 4/1993 |
| DE | 4306478 | 9/1994 |
| DE | 29504378 | 10/1995 |
| DE | 29715634 | 11/1997 |
| DE | 19722075 | 10/1998 |
| DK | 0064055 | 10/1945 |
| EP | 0 100 148 | 2/1984 |
| EP | 0 117 632 | 9/1984 |
| EP | 0 161 865 | 11/1985 |
| EP | 0 358 302 | 3/1990 |
| EP | 0 424 165 | 4/1991 |
| EP | 0 485 657 | 5/1992 |
| EP | 0 547 496 | 6/1993 |
| EP | 0 730 845 | 9/1996 |
| EP | 0 853 950 | 7/1998 |
| EP | 0 777 504 | 10/1998 |
| EP | 0 880 953 | 12/1998 |
| EP | 1 088 569 | 4/2001 |
| EP | 1 100 574 | 5/2001 |
| EP | 1 190 732 | 3/2002 |
| EP | 1 018 967 | 8/2004 |
| EP | 1 726 276 | 11/2006 |
| FR | 500253 | 3/1920 |
| FR | 1303238 | 7/1962 |
| GB | 3090 | 0/1902 |
| GB | 641061 | 8/1950 |
| GB | 692578 | 6/1953 |
| GB | 1549756 | 8/1979 |
| GB | 1584772 | 2/1981 |
| GB | 2195255 | 4/1988 |
| GB | 2197789 | 6/1988 |
| GB | 2220357 | 1/1990 |
| GB | 2235877 | 3/1991 |
| GB | 2307180 | 5/1997 |
| GB | 2329127 | 3/1999 |
| GB | 2333965 | 8/1999 |
| GB | 2336546 | 10/1999 |
| GB | 2342584 | 4/2000 |
| GB | 2344531 | 6/2000 |
| GB | 2351025 | 12/2000 |
| GB | 2356148 | 5/2001 |
| HU | 199304 | 1/1989 |
| HU | 51150 | 4/1990 |
| HU | 205557 | 4/1990 |
| HU | P9006526 | 1/1993 |
| HU | P9302966 | 7/1996 |
| HU | 76351 | 8/1997 |
| HU | 215563 | 8/1997 |
| HU | 1666 | 12/1999 |
| JP | 57-177758 | 11/1982 |
| JP | 4-129536 | 4/1992 |
| JP | H6-14995 | 1/1994 |
| JP | 6-327761 | 11/1994 |
| JP | H10-504484 | 5/1998 |
| JP | 2001-283352 | 10/2001 |
| JP | 2001-524850 | 12/2001 |
| SE | 0084485 | 10/1935 |
| SG | 71559 | 4/2002 |
| SU | 587941 | 1/1978 |
| SU | 1268175 | 11/1986 |
| WO | WO 80/02182 | 10/1980 |
| WO | WO 87/04626 | 8/1987 |
| WO | WO 89/04158 | 5/1989 |
| WO | WO 90/10424 | 9/1990 |

| | | |
|---|---|---|
| WO | WO 90/11795 | 10/1990 |
| WO | WO 91/00718 | 1/1991 |
| WO | WO 91/08793 | 6/1991 |
| WO | WO 91/16030 | 10/1991 |
| WO | WO 92/12750 | 8/1992 |
| WO | WO 92/19313 | 11/1992 |
| WO | WO 92/20299 | 11/1992 |
| WO | WO 93/09715 | 3/1993 |
| WO | WO 93/09727 | 5/1993 |
| WO | WO 94/00090 | 1/1994 |
| WO | WO 94/20041 | 9/1994 |
| WO | WO 96/05873 | 2/1996 |
| WO | WO 96/15745 | 5/1996 |
| WO | WO 97/18007 | 3/1997 |
| WO | WO 98/02205 | 1/1998 |
| WO | WO 98/38944 | 9/1998 |
| WO | WO 99/01173 | 1/1999 |
| WO | WO 99/13793 | 3/1999 |
| WO | WO 99/23990 | 5/1999 |
| WO | WO 99/59816 | 11/1999 |
| WO | WO 00/07653 | 2/2000 |
| WO | WO 00/15277 | 3/2000 |
| WO | WO 00/21586 | 4/2000 |
| WO | WO 00/26100 | 5/2000 |
| WO | WO 00/28890 | 5/2000 |
| WO | WO 00/30567 | 6/2000 |
| WO | WO 00/32247 | 6/2000 |
| WO | WO 00/38552 | 7/2000 |
| WO | WO 00/38755 | 7/2000 |
| WO | WO 00/42958 | 7/2000 |
| WO | WO 00/59418 | 10/2000 |
| WO | WO 00/59424 | 10/2000 |
| WO | WO 00/61206 | 10/2000 |
| WO | WO 00/64394 | 11/2000 |
| WO | WO 01/34223 | 5/2001 |
| WO | WO 01/37922 | 5/2001 |
| WO | WO 01/49233 | 7/2001 |
| WO | WO 01/85248 | 11/2001 |
| WO | WO 01/89431 | 11/2001 |
| WO | WO 02/38091 | 5/2002 |
| WO | WO 02/43634 | 6/2002 |
| WO | WO 03/005943 | 1/2003 |
| WO | WO 03/045492 | 6/2003 |
| WO | WO 03/057071 | 7/2003 |
| WO | WO 03/057307 | 7/2003 |
| WO | WO 03/101508 | 12/2003 |

OTHER PUBLICATIONS

Office Action issued in European Application No. 02 794 394.3, mailed Jun. 14, 2011.
Office Action issued in Japanese Application No. 2008-007788, mailed Jun. 28, 2011. (English translation).
Office Communication, issued in Japanese Patent Application No. 2009-236963, dated Aug. 2, 2011. (English translation).
Office Action issued in U.S. Appl. No. 12/328,531, mailed Jun. 13, 2011.
"Jump-Start Wound Healing with Oasis," Wounds, Special Supplement, 13(2):1-28, 2001.
"Oasis™ Wound Dressing," SIS™ Technology, pp. 1-4, Sep. 2001.
"Surgisis™ Soft-Tissue Graft," SIS™ Technology, pp. 1-4, Sep. 2001.
Abdullah, "A new method for fixation of drainage catheters," Journal of Hong Kong College of Radiologists, 4:272-273, 2001.
Advisory Action issued in U.S. Appl. No. 10/509,137, mailed Jun. 24, 2010.
Advisory Action issued in U.S. Appl. No. 10/885,431, mailed Dec. 8, 2009.
Advisory Action issued in U.S. Appl. No. 11/051,283, mailed May 5, 2010.
Advisory Action issued in U.S. Appl. No. 11/515,983, mailed Feb. 1, 2010.
Advisory Action issued in U.S. Appl. No. 11/761,066, mailed Feb. 16, 2010.
Argenta et al., "Vacuum-assisted closure: a new method for wound control and treatment: Clinical experience," Annals of Plastic Surgery, 38(6):563-577, 1997.
Argenta et al., Patent Application entitled "The enhancement of wound healing and flap survival by a new negative pressure device," 30 pages, 1997.
Arnljots and Svedman, "Irrigation Treatment in Split-Thickness Skin Grafting of Intractable Leg Ulcers," Scand J. Plast Reconstr. Surg., 19(2):211-213, 1985.
Bagautdinov, "Variant of external vacuum aspiration in the treatment of purulent diseases of soft tissues," Current Problems in Modern Clinical Surgery: Interdepartmental Collection, edited by V. Ye Volkov et al. (Chuvashia State University, Cheboksary, U.S.S.R. 1986);pp. 94-96.
Blackburn II et al.; "Negative-pressure dressings as a bolster for skin grafts," Annals of Plastic Surgery, 40(5):453-457, 1998.
Borzov et al., "Vacuum therapy of some skin diseases," Vestn. Dermatol. Venerol. (English translation), Aug. 1965.
Brochure—"Cavi-Care," Smith & Nephew, 2000.
Brochure—Aeros—Care-E-Vac; 2 pages, 1988.
Brochure—Aeros—Instavac Aspirator; 1 page, 1988.
Brochure—Aeros—Moblvacll, 1 page, 1988.
Brochure—Augustine Medical, Warm-Up Active Wound Therapy Wound Covers, 3 pages, 1999.
Brochure—Emerson Transport Suction Unit; 1 page, 1995.
Brochure—Healthpoint® Oasis® Wound Matrix, Cook Biotech Incorporated, 2003.
Brochure—Hiblow Air Pump; 1 page, 1999.
Brochure—KCI—The V.A.C. (Vacuum Assisted Closure), 7 pages, 1998.
Brochure—Microtek Heritage, Inc.—The Wound-Evac ET, Closed Wound Suction System, 4 pages, 1986.
Brochure—Pleur-evac Adult-Pediatric-Non-Metered Disposable "3-bottle" Unit, A-4000; 6 pages, 1995.
Brochure—Series 55—Emerson Post-Operative Suction Pumps; 1 page, 1996.
Brochure—Wells Johnson Company—Point 5 Aspirator; 2 pages, 1988.
Brochure/Instruction Manual—Creative Medical Laboratories, Inc.—TUGS (Transportable Universal Gradient Suction) System, 1984.
Bucalo et al., "Inhibition of cell proliferation by chronic wound fluid," Wound Repair and Regeneration, 181-186, 1993.
Chariker et al., "Effective management of incisional and cutaneous fistulae with closed suction wound drainage," Contemporary Surgery, 34:59-63, 1989.
Chinn and Burns, "Closed wound suction drainage," The Journal of Foot Surgery, 24(1):76-81, 1985.
Comment-Ruckley et al., "Vacuum drainage of groin wounds after vascular surgery," pp. 505-506, 1991.
Communication of Notice of Opposition issued in European Application No. 07001838.7, mailed Apr. 28, 2010.
Dattilo, Jr. et al.; "Medical textiles: application of an absorbable barbed bi-directional surgical suture"; Journal of Textile and Apparel, Technology and Management, 2(2):1-5, 2002.
Davydov et al., "Bacteriological and cytological assessment of vacuum therapy for purulent wounds," Vestnik Khirurgi, pp. 48-52 (and 8 page English translation thereof), Oct. 1988.
Davydov et al., "Basis of the use of forced early secondary suture in the treatment of suppurative wounds by the vacuum therapy method," Vestn. Khir. (English translation), Mar. 1990.
Davydov et al., "Concepts for the clinical-biological management of the wound process in the treatment of purulent wounds by means of vacuum therapy," Vestnik Khirurgi, pp. 132-136 (and 8 page English translation thereof), Jul. 1980.
Davydov et al., "Pathogenic mechanism of the effect of vacuum therapy on the course of the wound process," Khirurgiia, (English translation), Jun. 1990.
Davydov et al., "Vaccuum therapy in the treatment of acute suppurative diseases of soft tissues and suppurative wounds," Vestn. Khir. (English translation), Sep. 1988.
Davydov et al., "Vacuum Therapy in the Treatment of Purulent Lactation Mastitis," Vestnik Khirurgi, pp. 66-70 (and 9 page English translation thereof), May 1986.
Decision on Appeal issued in U.S. Appl. No. 10/276,778, mailed Mar. 6, 2010.

Decision on Appeal issued in U.S. Appl. No. 11/242,543, mailed Mar. 5, 2010.
Definition of "pore," provided by Merriam-Webster Online Dictionary, printed Apr. 5, 2010.
Definition of "porous," provided by Merriam-Webster Online Dictionary, printed Apr. 5, 2010.
Dunlop et al., "Vacuum drainage of groin wounds after vascular surgery: A controlled trial," Br. J. Surg., 77:562-563, 1990.
Egnell Minor, Instruction Book, First Edition, 300, 7502, pp. 24, Feb. 1975.
Egnell Minor: Addition to the Users Manual Concerning Overflow Protection—Concerns all Egnell Pumps, Feb. 3, 1983, pp. 2.
Fleischmann, "Vacuum sealing for treatment of problematic wounds," WundForum Spezial IHW (English translation), pp. 54-55, 1994.
Fleishmann et al., "Vacuum sealing for treatment of soft tissue injury in open fractures," Unfallchirurg, 96:488-492, 1993. (English translation of summary provided).
Fourth SIS-ECM Symposium, Phoenix, Arizona, Dec. 6-7, 2002.
Genecov et al., "A controlled subatmospheric pressure dressing increases the reate of skin graft donor site reepithelialization," Annals of Plastic Surgery, 40(3):219-225, 1998.
Greer et al., "The use of subatmospheric pressure dressing therapy to close lymphocutaneous fistulas of the groin," British Journal of Plastic Surgery, 53(6):484-487, 2000.
Jeter et al., "Managing draining wounds and fistulae: new and established methods," Chronic Wound Care, 27:240-246, 1990.
Johnson, "An improved technique for skin graft placement using a suction drain," Surgery, Gynecology, and Obstetrics, 159(6):584-585, 1984.
Kinetic Concepts, Inc., Form 10-K—Annual report pursuant to section 13 or 15(d) of the Securities Exchange Act of 1934, for the fiscal year ended Dec. 31, 2006, United States Securities and Exchange Commission, pp. 1, 2, 3, 12, 13, and 14.
Klein, "Cook Incorporated forms dedicated tissue engineered products group," PR Newswire, 2000.
Kostyuchenok et al., "Vacuum treatment in the surgical management of purulent wounds"; Vestnik Khirurgi, pp. 18-21 (and 6 page English translation thereof), Sep. 1986.
Kuznetsov and Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92, Oct. 1986.
Landis et al., "The effects of alternative suction and pressure on blood flow to the lower extremities," Alternate Suction and Pressure, pp. 925-961.
Letsou et al., "Stimulation of adenylate cyclase activity in cultured endothelial cells subjected to cyclic stretch," Journal of Cardiovascular Surgery, 31:634-639, 1990.
Letter and Memo reporting Office Action issued in Mexican Application No. PA/a/2001/001124, mailed Jul. 13, 2004.
Lundvall et al., "Transmission of externally applied negative pressure to the underlying tissue. A study on the upper arm of man," Acta Physiol. Scand., 136:403-409, 1989.
Masters, "Reliable, inexpensive and simple suction dressings," Letter to the Editor, British Journal of Plastic Surgery, Elsevier Science/The British Association of Plastic Surgeons, UK, 51(3):267, 1998.
McCarty, "Cook Incorporated forms dedicated tissue engineered products group," Cook® Online, News and Media Information, 2000.
Medical Industry Week, "KCI offers new treatment for non-healing wounds," 1 page, 1989.
Mendez-Eastman, "When wounds won't heal," RN, 61(1):20-24, 1998.
Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
Mirazimov et al., "Free skin graft of the foot with preparation of the wound surface by vacuum treatment," Ortop. Travmatol Protez. (English translation), Oct. 1966.

Morykwas et al., "Nonsurgical modalities to enhance healing and care of soft tissue wounds," www.sma.org/soa/jsoawt97, Feb. 11, 1999.
Morykwas et al., "Use of negative pressure to increase the rate of granulation tissue formation in chronic open wounds," Extracellular Matrix and Healing, p. 800, 1993.
Morykwas et al., "Vacuum-assisted closure: a new method for wound control and treatment: Animal studies and basic foundation," Annals of Plastic Surgery, 38(6):553-562, 1997.
Mulder et al., "Clinicians' pocket guide to chronic wound repair," Wound Healing Publications, 1991.
Nakayama et al., "A new dressing method for free skin grafting in hands," Ann. Plast. Surg., 26(5):499-502, 1991.
Nakayama et al., "A new method for the dressing of free skin grafts," Plast. Reconstr. Surg., 86(6):1216-1219, 1990.
Neumann et al., "Gelatin-based sprayable foam as a skin substitute," J. of Biomed Materials Research, 15:9-18, 1981.
Notice of Allowance issued in U.S. Appl. No. 10/276,778, mailed May 21, 2010.
Notice of Allowance issued in U.S. Appl. No. 10/276,778, mailed Sep. 7, 2010.
Notice of Allowance issued in U.S. Appl. No. 10/524,957, mailed Oct. 14, 2010.
Notice of Allowance issued in U.S. Appl. No. 10/664,535, mailed Jun. 2, 2010.
Notice of Allowance issued in U.S. Appl. No. 10/664,535, mailed Sep. 9, 2010.
Notice of Allowance issued in U.S. Appl. No. 10/885,431, mailed Mar. 22, 2010.
Notice of Allowance issued in U.S. Appl. No. 11/051,283, mailed Mar. 29, 2011.
Notice of Allowance issued in U.S. Appl. No. 11/230,988, mailed Dec. 3, 2010.
Notice of Allowance issued in U.S. Appl. No. 11/242,543, mailed Sep. 27, 2010.
Notice of Allowance issued in U.S. Appl. No. 11/515,983, mailed May 17, 2011.
Notice of Allowance issued in U.S. Appl. No. 11/761,066, mailed May 13, 2010.
Office Action issued in Australian Application No. 5255/99, mailed Aug. 6, 2002.
Office Action issued in Canadian Application No. 2,338,443, mailed Feb. 7, 2006.
Office Action issued in Canadian Application No. 2,390,131, mailed Jul. 20, 2007.
Office Action issued in Canadian Application No. 2,467,837, mailed May 27, 2009.
Office Action issued in Canadian Application No. 2,481,016, mailed Aug. 13, 2009.
Office Action issued in Canadian Application No. 2,481,016, mailed Jun. 15, 2010.
Office Action issued in Canadian Application No. 2,481,016, mailed Apr. 1, 2011.
Office Action issued in Czech Republic Application No. PV2001-497, mailed Feb. 7, 2001.
Office Action issued in European Application No. 00991498.7, mailed Dec. 17, 2003.
Office Action issued in European Application No. 00991498.7, mailed Jan. 2, 2006.
Office Action issued in European Application No. 01 998 292.5, mailed May 7, 2010.
Office Action issued in European Application No. 01998292.5, mailed Feb. 18, 2005.
Office Action issued in European Application No. 01998292.5, mailed Jul. 17, 2006.
Office Action issued in European Application No. 01998292.5, mailed Sep. 12, 2008.
Office Action issued in European Application No. 02 794 388.5, mailed Feb. 10, 2011.
Office Action issued in European Application No. 02 794 394.3, mailed Nov. 26, 2010.
Office Action issued in European Application No. 02 794 397.6, mailed Oct. 12, 2010.

Office Action issued in European Application No. 02784588.2, mailed Sep. 15, 2005.
Office Action issued in European Application No. 03 734 294.6, mailed Apr. 21, 2011.
Office Action issued in European Application No. 08010957.2, mailed Apr. 8, 2009.
Office Action issued in European Application No. 99 937 799, mailed Aug. 18, 2003.
Office Action issued in Japanese Application No. 2001-539532, mailed May 11, 2010 (and English language translation thereof).
Office Action issued in Japanese Application No. 2004-508861, mailed Apr. 14, 2009, and English language translation thereof.
Office Action issued in Japanese Application No. 2004-508861, mailed Feb. 16, 2010, and English language translation thereof.
Office Action issued in Japanese Application No. 2008-007788, mailed Oct. 5, 2010.
Office Action issued in Polish Application No. P-357 417, mailed Nov. 25, 2008; English translation.
Office Action issued in Polish Application No. P-364 754, 2006.
Office Action issued in U.S. Appl. No. 09/369,113, mailed Jan. 31, 2001.
Office Action issued in U.S. Appl. No. 09/725,352, mailed Dec. 12, 2002.
Office Action issued in U.S. Appl. No. 09/743,737, mailed Aug. 11, 2006.
Office Action issued in U.S. Appl. No. 09/743,737, mailed Apr. 1, 2003.
Office Action issued in U.S. Appl. No. 09/743,737, mailed Jun. 19, 2002.
Office Action issued in U.S. Appl. No. 09/743,737, mailed Oct. 23, 2002.
Office Action issued in U.S. Appl. No. 09/743,737, mailed Sep. 8, 2005.
Office Action issued in U.S. Appl. No. 09/855,287, mailed Dec. 15, 2003.
Office Action issued in U.S. Appl. No. 09/855,287, mailed Jul. 14, 2005.
Office Action issued in U.S. Appl. No. 09/855,287, mailed Jun. 24, 2004.
Office Action issued in U.S. Appl. No. 09/855,287, mailed Oct. 1, 2002.
Office Action issued in U.S. Appl. No. 09/994,537, mailed Jan. 16, 2003.
Office Action issued in U.S. Appl. No. 09/994,537, mailed Jun. 30, 2003.
Office Action issued in U.S. Appl. No. 10/144,504, mailed May 14, 2004.
Office Action issued in U.S. Appl. No. 10/267,358, mailed Jun. 29, 2005.
Office Action issued in U.S. Appl. No. 10/276,778, mailed Aug. 7, 2008.
Office Action issued in U.S. Appl. No. 10/276,778, mailed Apr. 24, 2006.
Office Action issued in U.S. Appl. No. 10/276,778, mailed Jul. 13, 2007.
Office Action issued in U.S. Appl. No. 10/276,778, mailed Mar. 22, 2007.
Office Action issued in U.S. Appl. No. 10/276,778, mailed Nov. 19, 2007.
Office Action issued in U.S. Appl. No. 10/276,778, mailed Oct. 11, 2006.
Office Action issued in U.S. Appl. No. 10/496,360, mailed Jun. 2, 2009.
Office Action issued in U.S. Appl. No. 10/496,360, mailed Jun. 12, 2006.
Office Action issued in U.S. Appl. No. 10/496,360, mailed Mar. 26, 2008.
Office Action issued in U.S. Appl. No. 10/496,360, mailed Mar. 14, 2007.
Office Action issued in U.S. Appl. No. 10/496,360, mailed Oct. 3, 2008.
Office Action issued in U.S. Appl. No. 10/496,360, mailed Oct. 5, 2006.
Office Action issued in U.S. Appl. No. 10/496,360, mailed Sep. 10, 2007.
Office Action issued in U.S. Appl. No. 10/496,623, mailed Jun. 9, 2006.
Office Action issued in U.S. Appl. No. 10/509,137, mailed Apr. 9, 2010.
Office Action issued in U.S. Appl. No. 10/509,137, mailed Apr. 28, 2011.
Office Action issued in U.S. Appl. No. 10/509,137, mailed Dec. 20, 2007.
Office Action issued in U.S. Appl. No. 10/509,137, mailed Dec. 8, 2010.
Office Action issued in U.S. Appl. No. 10/509,137, mailed Jun. 3, 2009.
Office Action issued in U.S. Appl. No. 10/509,137, mailed Jun. 22, 2007.
Office Action issued in U.S. Appl. No. 10/509,137, mailed Jan. 10, 2007.
Office Action issued in U.S. Appl. No. 10/509,137, mailed Nov. 24, 2008.
Office Action issued in U.S. Appl. No. 10/524,957, mailed Apr. 11, 2007.
Office Action issued in U.S. Appl. No. 10/524,957, mailed Aug. 10, 2007.
Office Action issued in U.S. Appl. No. 10/524,957, mailed Apr. 15, 2008.
Office Action issued in U.S. Appl. No. 10/524,957, mailed Aug. 3, 2009.
Office Action issued in U.S. Appl. No. 10/524,957, mailed Feb. 25, 2010.
Office Action issued in U.S. Appl. No. 10/524,957, mailed Jul. 26, 2010.
Office Action issued in U.S. Appl. No. 10/524,957, mailed Sep. 30, 2008.
Office Action issued in U.S. Appl. No. 10/664,535, mailed Apr. 17, 2008.
Office Action issued in U.S. Appl. No. 10/664,535, mailed Apr. 2, 2007.
Office Action issued in U.S. Appl. No. 10/664,535, mailed Dec. 15, 2009.
Office Action issued in U.S. Appl. No. 10/664,535, mailed Mar. 1, 2006.
Office Action issued in U.S. Appl. No. 10/664,535, mailed Oct. 26, 2007.
Office Action issued in U.S. Appl. No. 10/664,535, mailed Oct. 16, 2006.
Office Action issued in U.S. Appl. No. 10/885,431, mailed Apr. 15, 2008.
Office Action issued in U.S. Appl. No. 10/885,431, mailed Jun. 24, 2009.
Office Action issued in U.S. Appl. No. 10/885,431, mailed Mar. 22, 2007.
Office Action issued in U.S. Appl. No. 10/885,431, mailed Sep. 26, 2008.
Office Action issued in U.S. Appl. No. 10/885,431, mailed Sep. 19, 2007.
Office Action issued in U.S. Appl. No. 10/885,431, mailed Sep. 11, 2006.
Office Action issued in U.S. Appl. No. 10/997,612, mailed Apr. 30, 2007.
Office Action issued in U.S. Appl. No. 10/997,612, mailed Mar. 20, 2008.
Office Action issued in U.S. Appl. No. 10/997,612, mailed May 5, 2006.
Office Action issued in U.S. Appl. No. 10/997,612, mailed Nov. 14, 2008.
Office Action issued in U.S. Appl. No. 10/997,612, mailed Nov. 19, 2007.
Office Action issued in U.S. Appl. No. 10/997,612, mailed Oct. 31, 2006.
Office Action issued in U.S. Appl. No. 11/051,283, mailed Feb. 22, 2006.

Office Action issued in U.S. Appl. No. 11/051,283, mailed Feb. 25, 2010.
Office Action issued in U.S. Appl. No. 11/051,283, mailed Jun. 5, 2009.
Office Action issued in U.S. Appl. No. 11/051,283, mailed Jan. 9, 2008.
Office Action issued in U.S. Appl. No. 11/051,283, mailed Mar. 22, 2007.
Office Action issued in U.S. Appl. No. 11/051,283, mailed Oct. 17, 2008.
Office Action issued in U.S. Appl. No. 11/051,283, mailed Oct. 15, 2010.
Office Action issued in U.S. Appl. No. 11/051,283, mailed Sep. 7, 2007.
Office Action issued in U.S. Appl. No. 11/051,283, mailed Sep. 29, 2006.
Office Action issued in U.S. Appl. No. 11/051,283, mailed Sep. 7, 2005.
Office Action issued in U.S. Appl. No. 11/230,988, mailed Apr. 16, 2009.
Office Action issued in U.S. Appl. No. 11/230,988, mailed Aug. 26, 2009.
Office Action issued in U.S. Appl. No. 11/230,988, mailed Mar. 26, 2008.
Office Action issued in U.S. Appl. No. 11/230,988, mailed Mar. 13, 2007.
Office Action issued in U.S. Appl. No. 11/230,988, mailed May 26, 2010.
Office Action issued in U.S. Appl. No. 11/230,988, mailed Oct. 3, 2008.
Office Action issued in U.S. Appl. No. 11/230,988, mailed Oct. 15, 2010.
Office Action issued in U.S. Appl. No. 11/230,988, mailed Sep. 28, 2006.
Office Action issued in U.S. Appl. No. 11/230,988, mailed Sep. 10, 2007.
Office Action issued in U.S. Appl. No. 11/242,543, mailed May 18, 2007.
Office Action issued in U.S. Appl. No. 11/242,543, mailed Oct. 20, 2006.
Office Action issued in U.S. Appl. No. 11/242,543, mailed Oct. 25, 2007.
Office Action issued in U.S. Appl. No. 11/347,073, mailed Apr. 1, 2008.
Office Action issued in U.S. Appl. No. 11/515,983, mailed May 11, 2009.
Office Action issued in U.S. Appl. No. 11/515,983, mailed May 7, 2010.
Office Action issued in U.S. Appl. No. 11/515,983, mailed Nov. 20, 2009.
Office Action issued in U.S. Appl. No. 11/515,983, mailed Oct. 5, 2010.
Office Action issued in U.S. Appl. No. 11/684,989, mailed Dec. 29, 2009.
Office Action issued in U.S. Appl. No. 11/684,989, mailed Jul. 7, 2009.
Office Action issued in U.S. Appl. No. 11/684,989, mailed Jun. 29, 2010.
Office Action issued in U.S. Appl. No. 11/684,989, mailed Nov. 18, 2008.
PCT International Preliminary Examination Report issued in International Application No. PCT/US2001/44194, mailed Dec. 3, 2003.
PCT International Search Report issued in International Application No. PCT/GB1998/02713, mailed Jan. 8, 1999.
PCT International Search Report issued in International Application No. PCT/GB1995/01983, mailed Nov. 23, 1995.
PCT International Search Report issued in International Application No. PCT/GB1996/02802, mailed Apr. 29, 1997.
PCT International Search Report issued in International Application No. PCT/US2002/32221, mailed Feb. 5, 2003.
PCT International Search Report issued in International Application No. PCT/US2000/42333, mailed Aug. 3, 2001.
PCT International Search Report issued in International Application No. PCT/US2002/41210, mailed Oct. 28, 2003.
PCT International Search Report issued in International Application No. PCT/US1999/17877, mailed Oct. 27, 1999.
PCT International Search Report issued in International Application No. PCT/US2001/15611, mailed Sep. 5, 2001.
PCT International Search Report issued in International Application No. PCT/US2002/41229, mailed Jun. 30, 2003.
PCT International Search Report issued in International Application No. PCT/US2002/41300, mailed Jul. 31, 2003.
PCT International Search Report issued in International Application No. PCT/US2001/44194, mailed Dec. 9, 2002.
PCT International Search Report issued in International Application No. PCT/US2002/41228, mailed Jun. 30, 2003.
PCT International Search Report issued in International Application No. PCT/US2002/37814, mailed Apr. 7, 2003.
PCT International Search Report issued in International Application No. PCT/US2002/41231, mailed May 9, 2003.
PCT International Search Report issued in International Application No. PCT/US2002/41234, mailed Oct. 24, 2003.
PCT Written Opinion issued in International Application No. PCT/GB1996/02802, mailed Sep. 3, 1997.
PCT Written Opinion issued in International Application No. PCT/GB1998/02713, mailed Jun. 8, 1999.
PCT Written Opinion issued in International Application No. PCT/US1999/17877, mailed Aug. 20, 2001.
PCT Written Opinion issued in International Application No. PCT/US2000/42333, mailed Jun. 24, 2002.
Response to Opposition submitted in European Patent No. EP 1 772 160, filed Sep. 29, 2010.
Roget's New Millenium Thesaurus, First Edition (v 1.3.1), 2007.
Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967).
Sames, "Sealing of wounds with vacuum drainage," *Br. Med. J.*, 2(6096):1123, 1977.
Schein et al., "The 'Sandwich Technique' in the management of the open abdomen," *British Journal of Surgery*, 73:369-370, 1986.
Schneider et al., "A new and reliable method of securing skin grafts to the difficult recipient bed," *Plastic and Reconstructive Surgery*, pp. 1195-1198, 1998.
Search Report issued in Hungarian Application No. P0103545, mailed Oct. 29, 2001.
Search Report issued in Hungarian Application No. P0500055, mailed May 3, 2005.
Solovev et al., "Guidelines, the method of treatment of immature external fistulas in the upper gastrointestinal tract," editor-in-chief Prov. V.I. Parahonyak, S.M. Kirov Gorky State Medical Institute, Gorky, U.S.S.R., 1987.
Solovev, Dissertation Abstract, "Treatment and prevention of suture failures after gastric resection," S.M. Kirov Gorky State Medical Institute, Gorky, U.S.S.R., 1988.
Supplemental Notice of Allowability issued in U.S. Appl. No. 10/885,431, mailed Apr. 22, 2010.
Supplementary Search Report issued in European Application No. 02794393.5, mailed Aug. 1, 2006.
Supplementary Search Report issued in European Application No. 02796039.2, mailed Sep. 4, 2009.
Supplementary Search Report issued in European Application No. 02794388.5, mailed Jun. 16, 2009.
Supplementary Search Report issued in European Application No. 02794392.7, mailed Jun. 5, 2009.
Supplementary Search Report issued in European Application No. 02794394.3, mailed Apr. 6, 2009.
Supplementary Search Report issued in European Application No. 02794397.6, mailed Jan. 29, 2009.
Supplementary Search Report issued in European Application No. 07001838.7, mailed Mar. 5, 2007.
Supplementary Search Report issued in European Application No. 08010957.2, mailed Aug. 27, 2008.

Svedman et al., "A dressing system providing fluid supply and suction drainage used for continuous or intermittent irrigation," *Annals of Plastic Surgery*, 17(2):125-133, 1986.

Svedman, "A dressing allowing continuous treatment of a biosurface," *IRCS Medical Science: Biomedical Technology, Clinical Medicine, Surgery and Transplantation*, 7:221, 1979.

Svedman, "Irrigation treatment of leg ulcers," *The Lancet*, 2(8349):532-534, 1983.

Teder et al., "Continuous wound irrigation in the pig," *J. Invest. Surg.*, 3:399-407, 1990.

Tennant, "The use of hypermia in the postoperative treatment of lesions of the extremities and thorax," *Journal of the American Medical Association*, 64:1548-1549, 1915.

Tittel et al., "New standards in postoperative wound drainage," *Eingag und Annahme des Manuskripts*, pp. 104-107, 1987.

Tribble, "An improved sump drain-irrigation device of simple construction," *Archives of Surgery*, 105(3):511-513, 1972.

Valenta, "Using the vacuum dressing alternative for difficult wounds," *AIN*, pp. 44-45, 1994.

Viljanto et al., "Local hyperalimentation of open wounds," *Br. J. Surg.*, 63:427-430, 1976.

Wolthuis et al., "Physiological effects of locally applied reduced pressure in man," *Physiological Reviews*, 54(3):566-595, 1974.

Wood et al., "Foam elastomer dressing in the management of open granulating wounds: experience with 250 patients," *Br. J of Surg.*, 64:554-557, 1977.

Wooding-Scott et al., "No wound is too big for resourceful nurses," *RN*, pp. 22-25, 1988.

Yusupov et al., "Active wound drainage," *Vestnik Khirurgi*, 138(4) (and 7 page English translation thereof), 1987.

Živadinović et al., "Vacuum therapy in the treatment of peripheral blood vessels," *Timok Medical Journal*, 11:161-164, 1986.

Notice of Allowance issued in U.S. Appl. No. 11/684,989, mailed Nov. 8, 2010.

Notice of Allowance issued in U.S. Appl. No. 10/509,137, dated Dec. 7, 2011.

Office Communication issued in Canadian Patent Application No. 2,689,308, dated Dec. 19, 2011.

Office Communication issued in European Patent Application No. 01 998 292.5, dated Feb. 16, 2002.

Office Communication issued in U.S. Appl. No. 12/328,531, dated Jan. 6, 2012.

Office Communication issued in U.S. Appl. No. 12/328,531, dated Mar. 16, 2012.

Office Action issued in U.S. Appl. No. 11/761,066, mailed Dec. 13, 2007.

Office Action issued in U.S. Appl. No. 11/761,066, mailed Dec. 9, 2009.

Office Action issued in U.S. Appl. No. 11/761,066, mailed Jun. 2, 2009.

Office Action issued in U.S. Appl. No. 11/761,066, mailed Oct. 28, 2008.

Office Action issued in U.S. Appl. No. 11/761,066, mailed Sep. 25, 2007.

Office Communication, issued in U.S. Appl. No. 12/328,531, dated Jun. 13, 2011.

Olenius et al., "Mitotic activity in expanded human skin," *Plastic and Reconstructive Surgery*, pp. 213-215, 1993.

Oosterbroek et al., "A micromachined pressure/flow-sensor," *Sensor and Actuators*, 77(3):167-177, 1999. Abstract Only.

Orringer et al., "Management of wounds in patients with complex enterocutaneous fistulas," *Surgery, Gynecology & Obstetrics*, 165:79-80, 1987.

Patent Application entitled "Method of treating tissue damage and apparatus for same," 28 pages. (U.S. Patent No. 5,645,081 included as a reference).

PCT Declaration of Non-Establishment of International Search Report issued in International Application No. PCT/US2003/17099, mailed Nov. 7, 2003.

PCT International Preliminary Examination Report issued in International Application No. PCT/GB1996/02802, mailed Jan. 15, 1998.

PCT International Preliminary Examination Report issued in International Application No. PCT/US1999/17877, mailed Oct. 30, 2001.

PCT International Preliminary Examination Report issued in International Application No. PCT/US2000/42333, mailed Nov. 19, 2002.

US 6,216,701, 04/2001, Heaton et al. (withdrawn)

\* cited by examiner

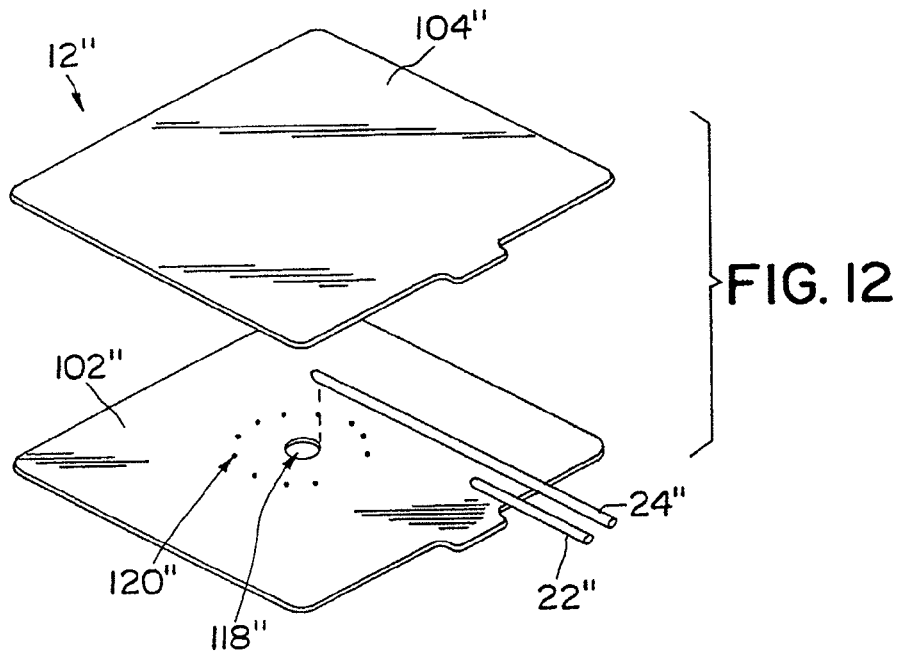
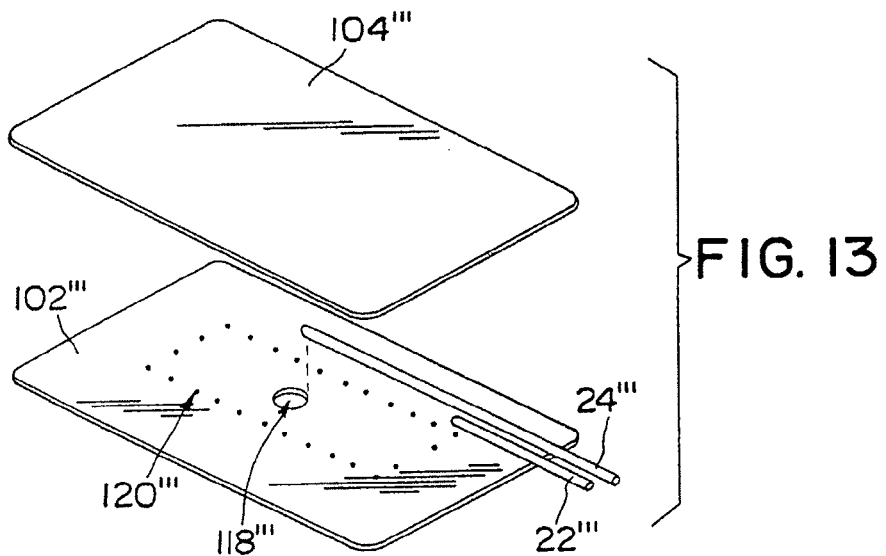

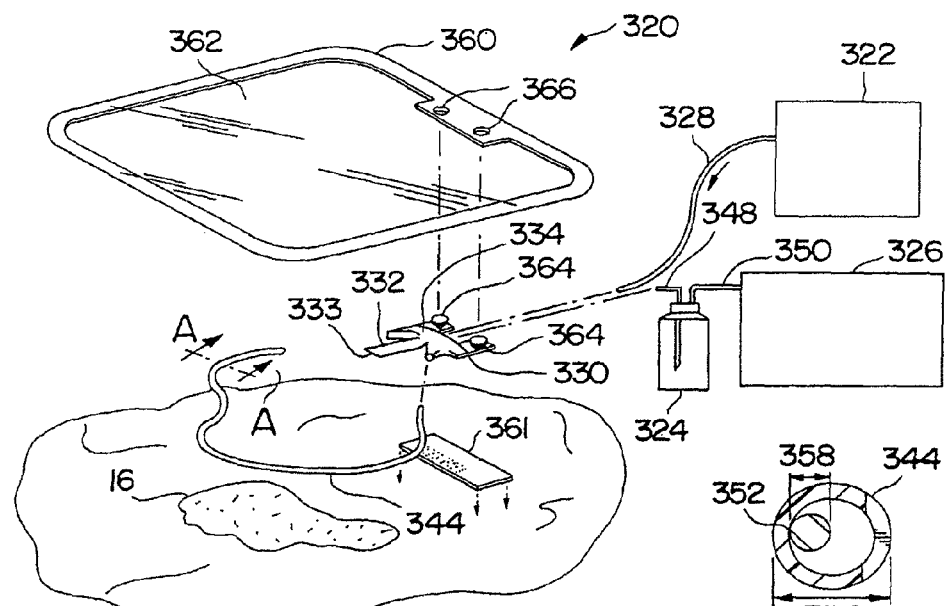
FIG. 20
FIG. 22
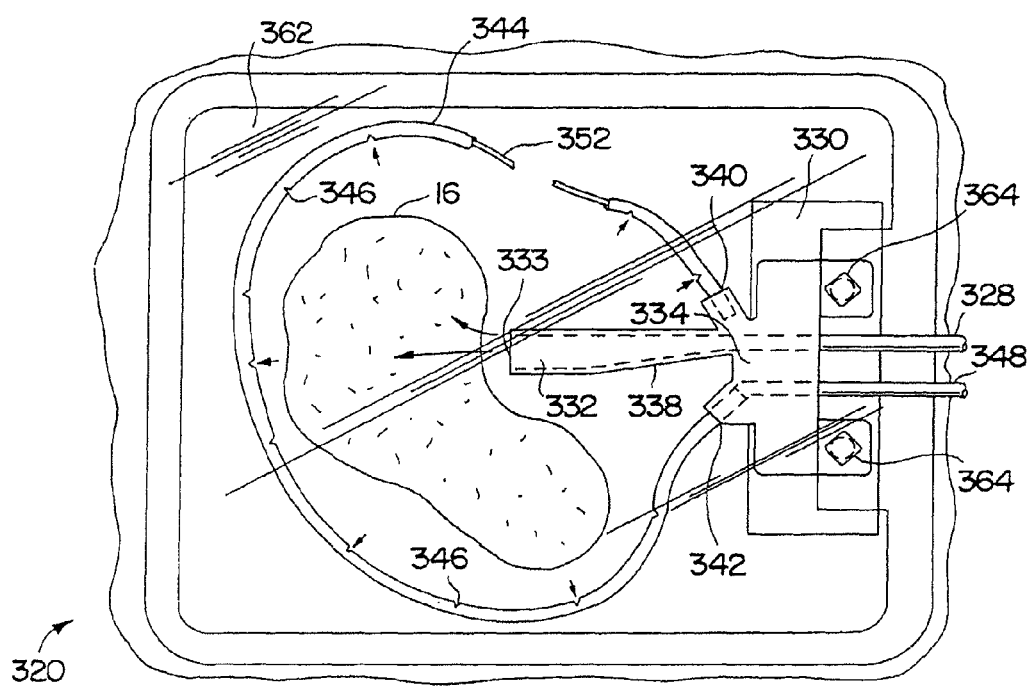
FIG. 21

WOUND TREATMENT APPARATUS

CROSS-REFERENCE TO RELATED APPLICATIONS

This application is a divisional application of U.S. patent application Ser. No. 11/761,066, filed Jun. 11, 2007, now U.S. Pat. No. 7,794,438; which is a divisional application of U.S. patent application Ser. No. 09/743,737, filed Jan. 16, 2001, now U.S. Pat. No. 7,276,051; which is a U.S. National Counterpart Application of International Patent Application, Serial No. PCT/US99/17877, filed Aug. 6, 1999; which claims priority to U.S. Provisional Patent Application Ser. No. 60/095,625, filed Aug. 7, 1998; and which claims priority to, and is a divisional application of U.S. patent application Ser. No. 09/369,113; filed Aug. 5, 1999, now U.S. Pat. No. 6,458,109. U.S. Provisional Patent Application No. 60/095,625, International Patent Application No. PCT/US99/17877, and U.S. patent application Ser. No. 09/369,113 are hereby expressly incorporated by reference herein.

TECHNICAL FIELD

The present invention relates to a wound treatment apparatus. More particularly, the present invention relates to a wound treatment apparatus for treatment of surface wounds.

BACKGROUND ART

Medical professionals such as nurses and doctors routinely treat patients having surface wounds of varying size, shape, and severity. Variations in wound type and other patient indications dictate variations in desired medications for treatment, such as antibiotics, growth factors, enzymes, hormones, insulin, anesthetics, and the like. The nature of a wound further prescribes variations in treatment protocols, such as delivery rates for medication and temperature control.

It is known that controlling the topical atmosphere adjacent a surface wound can enhance the healing process of the wound, for example by manipulating the oxygen content and/or humidity, or by providing hyperbaric oxygen as part of a treatment protocol, or by introducing medicinal agents adjacent the wound surface. See, for example, Madalene C. Y. Heng, *Topical Hyperbaric Therapy for Problem Skin Wounds,* 19 J. DERMATOL. SURG. ONCOL. 784 (1993); Theodor Kaufinan, M. D., et al., *The Microclimate Chamber: The Effect of Continuous Topical Administration of 96% Oxygen and 75% Relative Humidity on the Healing Rate of Experimental Deep Burns,* 23 J. TRAUMA 807 (1983); and U.S. Pat. No. 4,969,881 to Viesturs, entitled "Disposable Hyperbaric Oxygen Dressing." The medical industry would benefit from a practical system for surface wound treatment that provides medical professionals with a flexible way to control the topical atmosphere adjacent the wound, including application of aerosol medications and atmospheric constituents such as oxygen, as well as providing for collection of drainage from the wound site.

Several publications establish that surgeons were active years ago in applying a bandage or cover over a wound to provide a vacuum space above the wound to enhance healing. Nevertheless, Wake Forest University inventors, while not citing the publications, disclosed a vacuum wound therapy in U.S. Pat. Nos. 5,645,081 and 5,636,643.

Conventional treatment of a surface wound typically involves placement of a packing or dressing material, such as cotton gauze, directly in contact with the patient's wound. Often there is a need to change the dressing material frequently because it becomes saturated with effluent material discharged from the wound. The frequency of the need to change the dressing can increase when the care giver applies fluids to the dressing such as a saline solution, peroxide, topical antibiotics, or other medicines dictated by various treatment protocols for different types of wounds.

Changing a wound dressing poses several potential problems for the care giver. Inadvertent contact with sensitive tissue within and adjacent the wound can cause significant discomfort to the patient as well as further trauma to the wound. Exposing the wound to the open atmosphere can increase the chance of infection. Dressings are typically secured in place with adhesives, and thus changing the dressing requires removing the adhesive from the patient's skin, posing risks of pain and trauma to the patient, especially if there is necrotic tissue. Similarly, the dressing material can bind with tissue within the wound, so that changing the dressing can cause tissue loss from the wound, resulting in pain to the patient and retarding the healing process. Medical care givers and patients both would benefit from a bandage system that provides sanitary collection and disposal of material discharged from a wound in the course of the treatment and healing process while reducing the need to remove dressing or packing material placed in contact with the wound.

SUMMARY OF THE INVENTION

According to various features, characteristics, embodiments and alternatives of the present invention which will become apparent as the description thereof proceeds below, the present invention provides a wound treatment apparatus which includes a bandage configured to cover a wound and a seal about the perimeter of the wound. The bandage provides a cavity over the wound with a fluid supply and a fluid drainage in communication with the cavity. This cavity may be maintained at less than atmospheric pressure to enhance healing as known in the prior art. The present invention comprises enhancements to the prior art.

The wound treatment apparatus, for example, includes a first bandage configured to cover a wound. The first bandage includes a first surface configured to face toward the wound, at least one fluid delivery passageway through the first surface, at least one fluid drainage passageway through the first surface and fluid delivery conduit in communication with the fluid delivery passageway. The apparatus also includes a second bandage coupled with the first bandage. The second bandage includes a second surface configured to face toward the first bandage and provide a fluid space between the surfaces and has a fluid drainage conduit in communication with the fluid drainage passageway.

Another embodiment of the wound treatment apparatus includes a bandage including a wound facing surface configured to face toward the wound and a fluid drainage passageway having an opening adjacent the wound facing surface. A fluid drainage tube is coupled to the fluid drainage passageway. First and second fluid drainage receptacles are coupled to the drainage tube. First and second valves are coupled between the fluid drainage tube and the first and second fluid drainage receptacles, respectively.

An additional embodiment of the wound treatment apparatus includes a cover bandage configured to cover a wound and provide a seal on healthy skin tissue about the perimeter of the wound. The cover provides a relatively closed space about the wound which may be held at negative pressure. A fluid supply conduit is fitted between the cover bandage and healthy skin tissue near the wound. A fluid drainage conduit having at least one fluid drainage opening is fitted between the cover bandage and the healthy skin tissue and positioned on healthy skin tissue about the wound and the fluid supply.

A further embodiment of the wound treatment apparatus includes a cover bandage providing a closed seal about a wound and a relatively closed cavity over the wound to be held at a negative pressure. The cover bandage includes a first surface configured to face toward the wound having least one fluid delivery passageway disposed through the first surface, and at least one fluid drainage passageway disposed through the first surface. A second surface is configured to face toward the first surface and provide a fluid space between the surfaces. The fluid space is segregated into a first chamber and a second chamber, wherein the first chamber is formed about the fluid delivery passageway and the second chamber is formed about the fluid drainage passageway. A fluid delivery conduit is in fluid communication with the first chamber and the fluid delivery passageway. A fluid drainage conduit has at least one fluid drainage opening in fluid communication with the second chamber and the fluid drainage passageway.

A still further wound treatment apparatus includes a cover bandage providing a closed seal about a wound positioned on a joint having a cavity over the wound sized to receive the joint and to be held at a negative pressure. The cover bandage includes a first surface configured to face toward the wound, at least one fluid delivery passageway through the first surface, and a second surface configured to face toward the first surface providing a fluid space between the surfaces. A fluid delivery conduit is in fluid communication with the fluid space and the fluid delivery passageway. A fluid drainage conduit having at least one fluid drainage opening is also in fluid communication with the cavity.

Within the present invention, in combination with such a cover bandage, the fluid delivery to the wound may include nebulizers, liquid medication pumps, recirculating temperature regulated fluid tubes, heaters, temperature and pressure sensors, control valves, oxygen supplies, and controllers as described and claimed hereinafter. All of these features, including the vacuum feature, may be programmed to occur on prearranged schedules to deliver care-giver established protocols.

Additional features of the invention will become apparent to those skilled in the art upon consideration of the following detailed description exemplifying the best mode of carrying out the invention as presently perceived.

BRIEF DESCRIPTION OF THE DRAWINGS

The present invention will be described with reference to the attached drawings which are given as non-limiting examples only, in which:

FIG. 12 is a perspective view of another alternative embodiment of a bandage assembly;

FIG. 13 is a perspective view of yet another alternative embodiment of a bandage assembly;

FIG. 20 is an exploded view of a wound treatment assembly and a medicinal fluid supply system including an additional embodiment of the present invention;

FIG. 21 is a top view of the wound treatment assembly from FIG. 20;

FIG. 22 is a sectional view of the circulating fluid tube from the wound treatment assembly of FIG. 20, taken along line A-A;

DETAILED DESCRIPTION OF DRAWINGS

Figure 1:
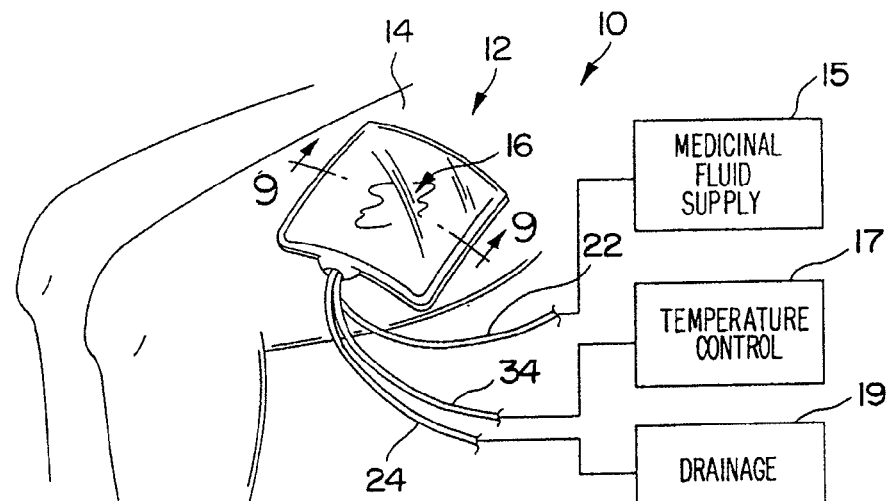
FIG. 1 is a perspective view of a wound treatment apparatus according to the present invention.

Referring now to the drawings, FIG. 1 illustrates a wound treatment apparatus 10 that includes a bandage assembly 12 coupled to a patient's skin 14 adjacent a surface wound 16. Apparatus 10 includes a wound temperature control system 17, a wound drainage system 19, and a medicinal fluid supply system 15 including a nebulizer 26 shown in FIGS. 2 and 3. Wound treatment apparatus 10 provides a system for controlling the topical atmosphere adjacent wound 16, including delivery of medication, control of atmospheric constituents, temperature regulation, and collection of wound drainage.

Including a nebulizer 26 (see FIGS. 2 and 3) in wound treatment apparatus 10 provides for delivering nebulized fluid containing dissolved wound treatment constituents, such as oxygen or medication, to the wound. As a wound heals it develops a liquid layer on its external surface. This liquid layer forms a barrier that impedes flow of atmospheric constituents, such as oxygen or medication, to the cells in the wound, because these constituents must diffuse through the liquid layer. Application of nebulized fluid improves treatment and healing because the nebulized fluid can readily mix with the liquid layer. This allows the dissolved constituents in the nebulized fluid to be readily diffused through the liquid layer and absorbed into the cells below.

Bandage assembly 12 is a two-part assembly that includes a fluid medication delivery bandage 18 and an adsorbent drainage bandage 20. Drainage bandage 20 is configured to be removably coupled to delivery bandage 18 as shown, for example, in FIGS. 2 and 3. Delivery bandage 18 provides for sealing the wound site from the ambient atmosphere so that supply system 15, temperature control system 17, and drainage system 19 can regulate the wound environment. By providing a two-piece, removably coupled bandage arrangement, bandage assembly 12 allows for changing the drainage bandage without the need to remove delivery bandage 18 from the patient's skin 14.

Delivery bandage 18 includes a medicinal fluid supply tube 22 and is coupled to the patient's skin 14 over wound 16. Delivery bandage 18 can remain in place while drainage bandage 20 can be changed as needed during wound treatment. Drainage bandage 20 includes a wound drainage tube 24 that is coupled to wound 16 through delivery bandage 18 to allow fluid from wound 16 to exit from bandage assembly 12, the fluid including both fluids secreted by wound 16 as well as fluids entering bandage 18 through medicinal fluid supply tube 22. Bandage assembly 12 thus allows control of the topical atmosphere adjacent wound 16 while limiting the exposure to atmospheric contaminants, allowing for use of treatment protocols to enhance healing while reducing opportunities for potential infection and trauma.

Figure 2:
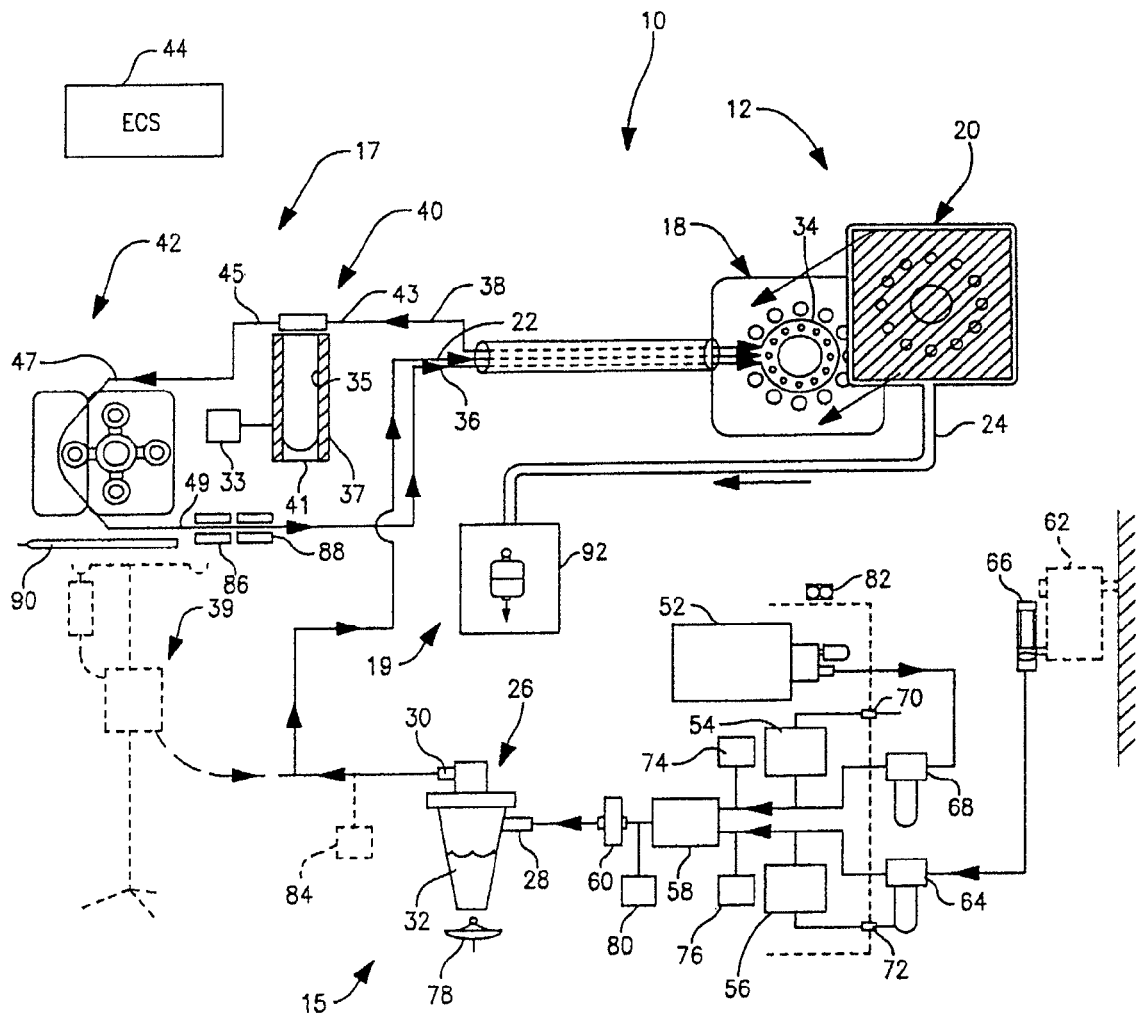
FIG. 2 is a schematic block diagram of a wound treatment apparatus according to the present invention.
Figure 3:
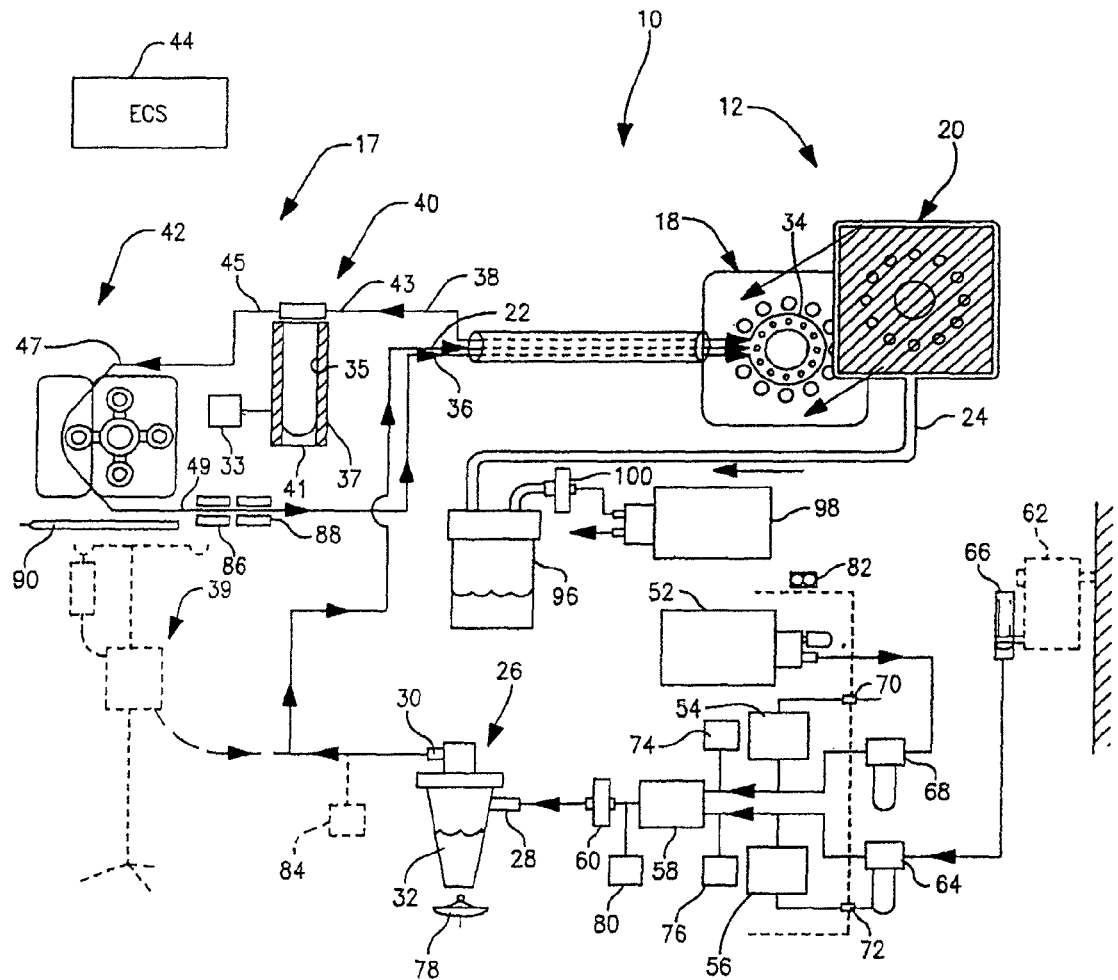
FIG. 3 is a schematic block diagram of an alternative embodiment wound treatment apparatus.

Medicinal fluid supply system 15 of wound treatment apparatus 10 illustratively includes nebulizer 26 and an optional liquid medication pump 39 as shown in FIGS. 2 and 3. Temperature control system 17 includes a heater 40 and pump 42. Drainage system 19 includes a drainage bag 92 as shown in FIG. 2 or alternatively a vacuum pump 98 and liquid trap bottle 96 as shown by 19' in FIG. 3.

Nebulizer 26 includes an input port 28 for accepting a nebulizer gas input, such as standard air or pure oxygen, a nebulized fluid output port 30, and a liquid reservoir 32 coupled between input and output ports 28, 30. Liquid reservoir 32 illustratively contains medication as needed to implement a treatment protocol for wound 16, such as antibiotics, growth factors, enzymes, hormones, insulin, anesthetics, and the like. It is understood that reservoir 32 can contain any fluid, such as pure water or a saline solution. Nebulizer 26 is illustratively a Mini Heart model manufactured by Vortran, which can atomize approximately 4 milliliters per hour of liquid medication at an input gas flow rate of approximately 1.5 liters per minute. It is understood, however, that any suitable nebulizing device can be used.

Nebulizer output port 30 is coupled to medicinal fluid supply tube 22 of delivery bandage 18 of bandage assembly 12. Optionally, a liquid medication pump 39 such as an IV pump can also be coupled to medicinal fluid supply tube 22.

Wound treatment apparatus 10 thus provides for delivery of either aerosol or liquid medication or both to wound 16 through delivery bandage 18.

As discussed in more detail below, delivery bandage 18 further includes a recirculating fluid tube 34 having an input port 36 and an output port 38. Wound treatment apparatus 10 includes a heater 40 and a peristaltic pump 42 coupled between the input and output ports 36, 38 of recirculating fluid tube 34. Temperature control system 17 thus allows temperature controlled liquid to flow through bandage assembly 12 to regulate the temperature at the site of wound 16.

Peristaltic pump 42 is illustratively a Model 313 manufactured by Watson Marlow, using a nominal flow rate of between 200 to 250 milliliters per minute. Although a peristaltic pump driven by an AC synchronous motor at 72 RPM is used because its disposable tubing elements eliminate the need to clean the pump between patient uses, it is understood that other pump designs such as centrifugal, gear-driven, or diaphragm type pumps can be used.

Heater 40 illustratively is a specially designed tubular unit that includes a tubular housing 37, a 100 watt heater element 35 positioned within housing 37, and a thermocouple 33 for monitoring the temperature of heater element 35. A fluid reservoir 41 is configured to fit within housing 37 so that heater element 35 can heat the recirculating fluid. As discussed below, other suitable heating systems can be used.

Fluid reservoir 41 illustratively is formed from a rubber silicone tube configured to fit snugly within housing 37. Reservoir 41 advantageously is provided as a prepackaged unit with bandage assembly 12 along with associated tubes to prevent spillage that can accidentally occur if an open container is used for the recirculating fluid. It is understood, however, that other suitable devices for controlling the temperature of the recirculating fluid can be used, such as an immersion heater configured to be placed within an open fluid reservoir (not shown), or alternative embodiment heating assembly 200 as shown in FIGS. 14-18 and discussed in detail below.

Wound treatment apparatus 10 further includes a computer-based electronic control system 44 that is coupled electronically to the electronic and electro-mechanical components such as nebulizer 26, peristaltic pump 42, heater 40 and thermocouple 33. Control system 44 provides for automated control of wound treatment apparatus 10 for various treatment protocols, for example to regulate temperature at the wound site by using heater 40 and pump 42 to regulate recirculating fluid temperature to 37° Celsius.

Control system 44 illustratively is directly coupled to the controlled components using analog, discrete, and serial I/O signals as required by the various component interfaces. It is understood that the communication mechanism can include any type of electronic network, such as any serial bus or parallel bus architecture. The communications protocol similarly can vary. For example, master-slave, token ring, or peer-to-peer communication protocols, such as Ethernet or Echelon LONworks™, can be used. By providing software control of wound treatment apparatus 10 components such as nebulizer 26, heater 40, and pump 42, control system 44 can automatically control the delivery of aerosol medication, temperature, and oxygen concentration levels at the site of wound 16 to implement a desired treatment protocol and to provide an optimal wound healing environment.

Nebulizer input port 28 is coupled to a nebulizer gas input assembly 46 that includes air and oxygen input ports 48, 50, an air compressor 52, air and oxygen pressure regulators 54, 56, a selector valve 58, and a nebulizer gas input filter 60. Filter 60 is illustratively a single use disposable bacteria filter.

Oxygen input port 50 can illustratively be coupled to a standard hospital oxygen blender 62 through a standard hospital air filter and water trap 64. An internal compressed oxygen supply (not shown) can replace oxygen blender 62. Oxygen filter and water trap 64 contains a 5 micron filter element and catch basin to trap particulate matter and condensed water output from oxygen blender 62. Blender 62 further illustratively includes an oxygen flowmeter 66 such as a standard hospital pediatric flowmeter that allows a flow set range of, for example, between zero and three liters per minute.

Air compressor 52 is coupled to nebulizer air input port 48 through an external air filter and water trap 68. Similar to supply of oxygen, an external compressed air supply (not shown) can also be used. Air compressor 52 is illustratively a diaphragm type pump driven by a brushless DC motor that can deliver a minimum of 1.3 liters per minute at 15 psi. Compressor 52 includes an input filter (not shown) having a 25 micron filter/silencer. Similar to oxygen filter and water trap 64, air filter and water trap 68 contains a 5 micron filter element and catch basin for trapping particulate matter and water droplets from the compressed air output from compressor 52.

Air and oxygen input ports 48, 50 are coupled to selector valve 58 through air and oxygen pressure regulators 54, 56, respectively. Regulators 54, 56 maintain air and oxygen pressure between about 15 and about 17 psi. Air pressure regulator 54 vents excess air outside of wound treatment apparatus 10 through an air vent 70 and oxygen pressure regulator vents through oxygen vent 72.

Selector valve 58 is coupled electronically to control system 44 to allow for software control of the mixing of air and oxygen so that the gas input to nebulizer 26 can range from pure air to pure oxygen. Selector valve 58 can eliminate the need for external oxygen blender 62. Selector valve 58 illustratively switches between air and oxygen at a predetermined rate, although other valve arrangements can be used to mix air and gas, such as a dual input mixing valve, a pair of butterfly valves or other valve configurations for mixing two fluid input streams. Control system 44 can be used to supply an air/oxygen treatment protocol to the wound site automatically. For instance, control system 44 can implement a programmed protocol to deliver 3 hours of air followed by 3 hours of oxygen, and so on, to the wound site. Valve 58 automatically switches to implement the programmed protocol.

Nebulizer gas input assembly 46 further includes an air pressure sensor 74 coupled between selector valve 58 and air pressure regulator 54, an oxygen pressure sensor 76 coupled between selector valve 58 and oxygen pressure regulator 56, and a nebulizer gas input pressure sensor 80 coupled between selector valve 58 and nebulizer input port 28. Sensors 74, 76, 80 are coupled to control system 44 to provide feedback for monitoring of proper system operation and so that an alarm can be indicated and wound treatment apparatus 10 shut down automatically if a pressure signal exceeds a predetermined threshold.

Wound treatment apparatus 10 also includes a nebulizer empty sensor 78 to indicate if nebulizer 26 is empty. Nebulizer empty sensor 78 provides a feedback signal to electronic control system 44 and illustratively is an acoustical sensor. Control system 44 continuously monitors the output signal from sensor 78, which changes distinctively when reservoir 32 becomes empty, at which point an alarm can be signaled and wound treatment apparatus 10 shut down. It is understood that other types of sensors can be used to determine if nebulizer 26 is empty, such as, for example, capacitive sensors, float switches, or optical, infrared, or ultrasonic sensors.

Wound treatment apparatus 10 further includes a nebulizer pressure sensor 80 coupled between selector valve 58 and nebulizer input port 28. Pressure sensor 80 provides a feedback signal to control system 44 indicative of pressure within nebulizer 26 and is also used to verify the proper operation of selector valve 58. Wound treatment apparatus 10 furthermore includes a tilt sensor 82 and a bandage interface pressure sensor 84, both coupled to control system 44. Tilt sensor 82 signals an alarm and shuts down apparatus 10 if apparatus 10 is tilted beyond a predetermined threshold, illustratively 30°.

Bandage interface pressure sensor 84 is coupled between nebulizer output port 30 and medicinal fluid supply tube 22 of bandage assembly 12. By monitoring back pressure from the bandage, pressure sensor 84 allows control system 44 to provide a display indicative of pressure at the interface between delivery bandage 18 or between the patient and a bed when the patient is lying directly on bandage assembly 12. Control system 44 can also signal an alarm and shut down apparatus 10 if interface pressure exceeds a predetermined threshold.

Pressure on a wound can cause further skin breakdown, especially if the wound is a decubitus ulcer or bed sore. The wound interface pressure from sensor 84 can be used as a feedback signal to a bed control or a support surface control to adjust a therapy surface. Sensor output 84 can also signal the care giver through the control system and a nurse call system so that the care-giver can move the patient, either on the existing mattress or to a reduced pressure support surface, for treating the wound.

Temperature control system 17 includes heater 40, reservoir 41, and pump 42. Fluid reservoir 41 includes an input port 43 coupled to output port 38 of recirculating fluid tube 34 and an output port 45 coupled to a tube feeding peristaltic pump 42.

Peristaltic pump 42 includes a pump input port 47 coupled to reservoir output port 45 and a pump output port 49 coupled to input port 36 of recirculating fluid tube 34. A pump output temperature sensor 86 and a pump safety shutoff temperature sensor 88 both are coupled between pump port 49 and recirculating fluid input port 36 of bandage assembly 12.

Pump output temperature sensor 86 provides a feedback to control system 44 for closed loop control of heater 40 to control fluid input temperature to tube 34 in bandage assembly 12 to a desired temperature, illustratively 37° Celsius. Safety shutoff temperature sensor 88 is similarly provided as a feedback to control system 44 and is used to disable and alarm apparatus 10 if recirculating fluid temperature exceeds a safe limit, such as 41° Celsius. Sensors 86, 88 illustratively are non-contact, infrared sensors such as an IRt/c.01HB-J-37C sensor from Exergen Corp., although it is understood that other suitable sensors can be used.

Optionally, proximity sensors (not shown) can be used to ensure that temperature sensors 86, 88 are properly coupled. For example, temperature sensors 86, 88 and respective proximity sensors can be coupled to a housing or channel into which a tube from recirculating fluid supply input port 36 is installed. If the proximity sensors do not detect the tube's presence within the channel, control system 44 can react accordingly, such as by providing a suitable display and/or alarm and/or by shutting down the system.

Temperature control system 17 further includes a liquid leak sensor 90 coupled adjacent pump 42 to monitor leaks from pump 42 or adjacent tubing. Sensor 90 is illustratively a capacitive sensor pad located under peristaltic pump 42. Sensor 90 provides a signal to electronic control system 44, which can alarm and disable wound treatment apparatus 10 if a leak is detected.

Wound treatment apparatus 10 further includes a wound effluent drainage receptacle or bag 92 that collects fluid flowing from bandage assembly 12 out of drainage tube 24, including both fluid supplied into bandage assembly 12 from supply tube 22 and discharge from wound 16. Drainage bag 92 includes a vapor filter 94 to filter gaseous components of fluid exiting bandage assembly 12. Vapor filter 94 is illustratively a standard hospital ventilator exhaust filter configured to plug directly into the side of drainage bag 92.

An alternative embodiment wound treatment apparatus 10' is shown in FIG. 3. Apparatus 10' replaces wound effluent drainage bag 92 and vapor filter 94 of apparatus 10 with a liquid trap bottle 96, a vacuum pump 98, and a vacuum filter 100 coupled between trap bottle 96 and pump 98. Liquid trap bottle 96 is coupled to drainage tube 24 to collect liquids in the fluid flow from bandage assembly 12. Vacuum pump 98 is used to apply a negative pressure to facilitate drainage. If desired, sufficient negative pressure can be applied so that negative pressure on the wound facilitates its closure. Filter 100 illustratively is a hydrophobic bacteria filter coupled between trap bottle 96 and vacuum pump 98.

Referring now to FIGS. 4-10, bandage assembly 12 includes delivery bandage 18 and drainage bandage 20. Delivery bandage 18 includes bottom and top sheets 102, 104 that sandwich both medicinal fluid supply tube 22 and recirculating fluid tube 34. Drainage bandage 20 includes bottom and top sheets 106, 108 that sandwich an adsorbent pad 110 and drainage tube 24. Adsorbent pad 110 is illustratively formed from medical grade hydrophilic foam, although any suitable material such as an absorbent substance can be used. Bandage sheets 102, 104, 106, 108 are illustratively formed from clear, flexible polyurethane or vinyl that meets USP Class VI requirements for medical applications.

Figure 5:
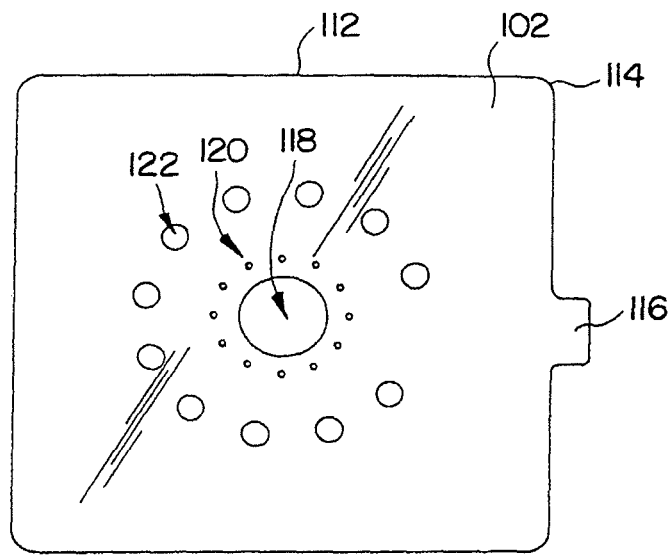
FIG. 5 is a top view of the bottom sheet of the medicinal delivery bandage of FIG. 4.

Delivery bandage bottom sheet 102 is formed with a generally square perimeter 112 having rounded corners 114 and a tab 116 along a side of perimeter 112 as best shown in FIG. 5. Bottom sheet 102 further includes a central wound drainage passageway 118, a plurality of medicinal fluid supply passageways 120 arranged in a circular pattern concentric with passageway 118, and a plurality of outer wound drainage passageways 122 arranged in another concentric circular pattern radially outward of delivery passageways 120. Delivery passageways 120 provide for delivery of fluid medications from medicinal fluid supply tube 22 to wound 16 and illustratively are relatively smaller than drainage passageways 118, 122 that provide for passage of wound drainage through delivery bandage 18.

Figure 6:
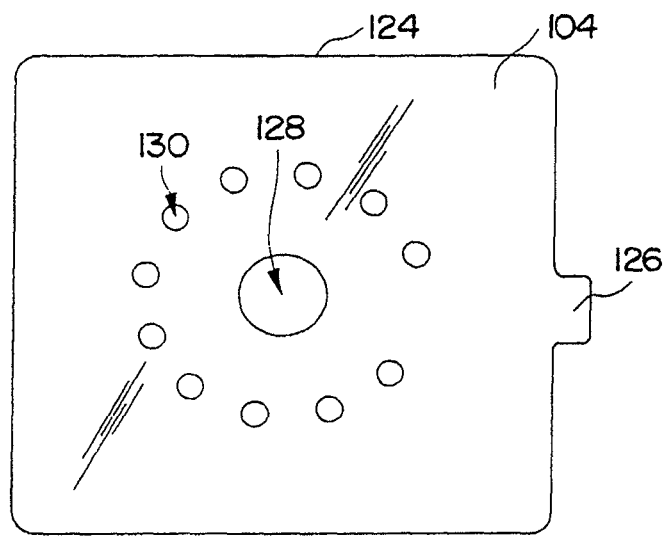
FIG. 6 is a top view of the top sheet of the medicinal delivery bandage of FIG. 4.

Delivery bandage top sheet 104 is formed to include a perimeter 124, tab 126, central passageway 128, and outer passageways 130 that are configured to align with perimeter 112, tab 116, central passageway 118, and outer passageways 122 of bottom sheet 102 as best shown in FIG. 6. When top and bottom sheets 102, 104 are aligned, central passageways 118, 128 and outer passageways 122, 130 are in fluid communication and allow wound effluent to pass through bandage 18.

Figure 7:
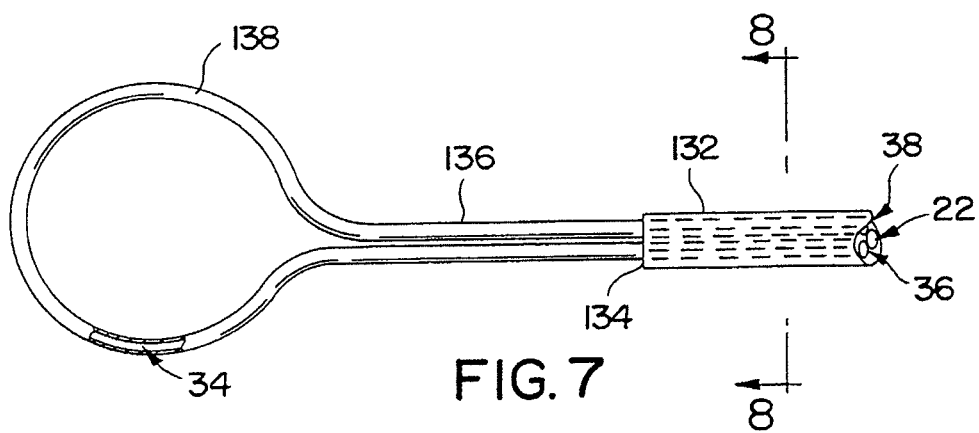
FIG. 7 is a top view of the medicinal fluid supply and temperature controlled, recirculating fluid tubes of FIG. 4.
Figure 8:
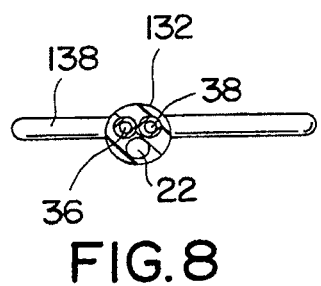
FIG. 8 is an end view of the medicinal fluid supply and temperature controlled, recirculating fluid tubes of FIG. 7.

Medicinal fluid supply tube 22 and recirculating fluid tube 34 illustratively are contained within a multi-lumen tube 132 as best shown in FIGS. 7 and 8. It is understood that separate tubes can be used. Multi-lumen tube 132 is a 65 durometer USP Class VI polyvinyl chloride triple lumen tube and has three channels, one of which defines supply tube 22 and the other two define portions of recirculating fluid tube 34. Tube 132 includes a terminal end 134 that defines an end of medicinal fluid supply tube 22.

Recirculating fluid tube 34 further includes a straight segment 136 that extends axially outward from end 134 and a generally circular segment 138 coupled to straight segment 136 as best shown in FIG. 7. The geometry of recirculating fluid tube 34 can vary as needed to distribute temperature controlled fluid throughout delivery bandage 18. Temperature regulated fluid, illustratively water, is circulated through delivery bandage 18 in segments 136, 138 from temperature control system 17 to maintain bandage 18 at an optimal temperature for wound treatment. It is understood that the temperature of bandage 18 can be regulated by control system 44 according to a desired treatment protocol, for example by maintaining a temperature to maximize treatment effectiveness of an enzyme or other medicinal fluid supplied through medicinal fluid supply tube 22.

Figure 10:
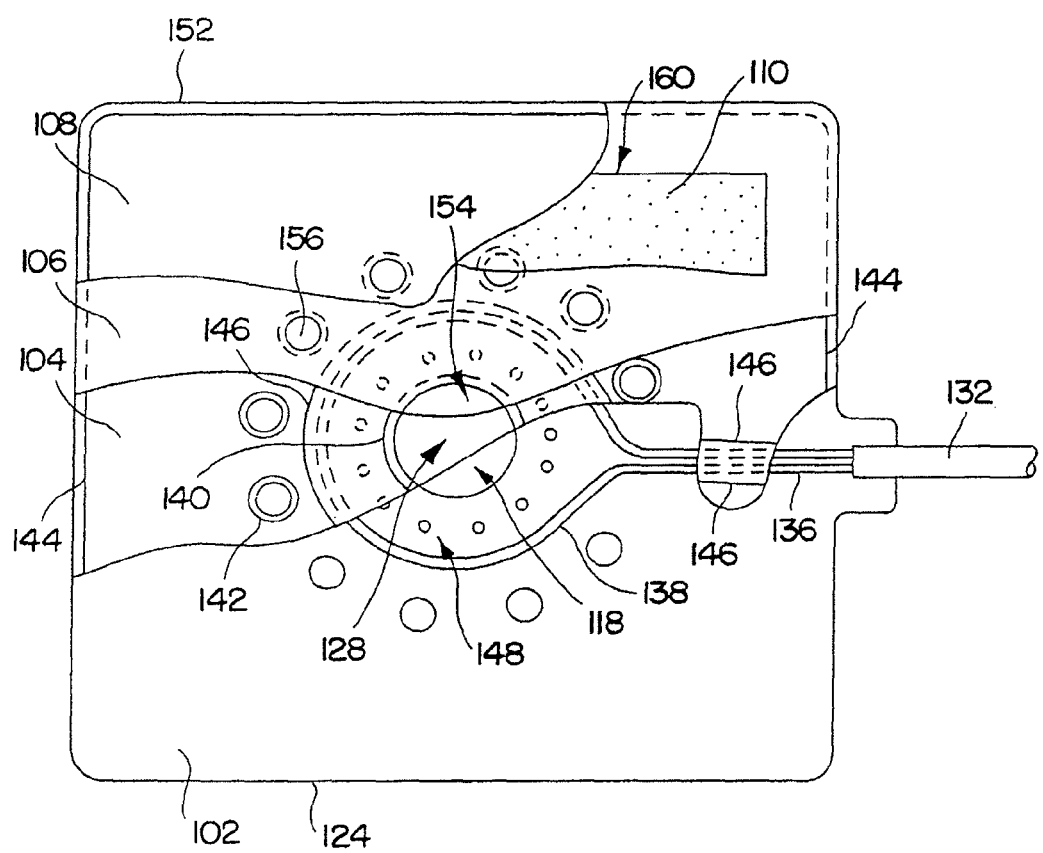
FIG. 10 is a top view of the bandage assembly of FIG. 1 with portions broken away.

Delivery bandage 18 is formed by sandwiching multi-lumen tube 132 between top and bottom sheets 102, 104 so that tube 132 extends over tabs 116, 126 and circular segment 138 is concentric with central passageways 118, 128 as best shown in FIG. 10. Top and bottom sheets 102, 104 are bonded together by radio frequency (RF) welding. Circular RF welds 140, 142 seal the perimeter around each pair of aligned wound drainage passageways 118, 128, and 122, 130. A perimeter RF weld 144 seals the aligned perimeters 112, 124.

A fluid delivery chamber weld 146 extends from perimeter weld 144 and encompasses inner wound drainage passageway weld 140 to define a fluid delivery chamber 148 that is in fluid communication with delivery passageways 120 in bottom sheet 102 and terminal end 134 of medicinal fluid supply tube 22. Thus, aerosol or liquid medications supplied through medicinal fluid supply tube 22 from nebulizer 26 or medicinal pump 39 can be delivered through delivery bandage 18 to wound 16 through chamber 148 that is isolated from wound drainage passageways 118, 122, 128, 130. Recirculating fluid tube 34 illustratively is contained within delivery chamber 148, although it is understood that tube 34 could be isolated from chamber 148.

Figure 4:
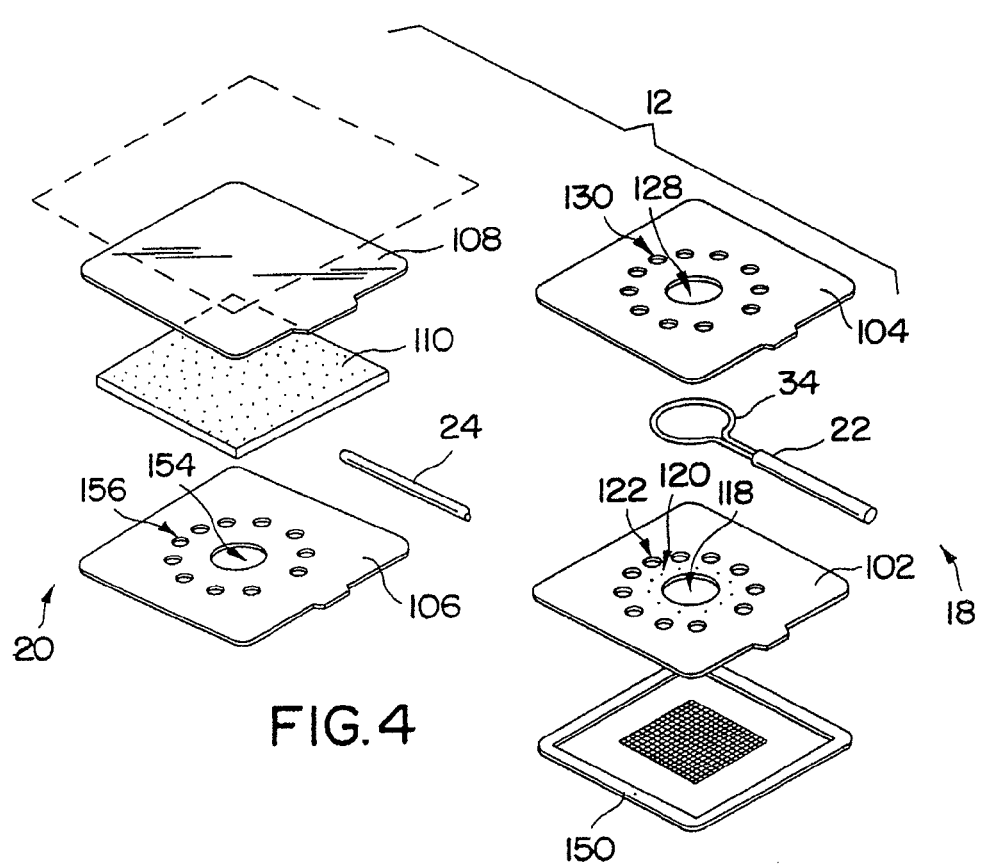
FIG. 4 is an exploded perspective view of a two-piece bandage assembly according to the present invention.
Figure 9:
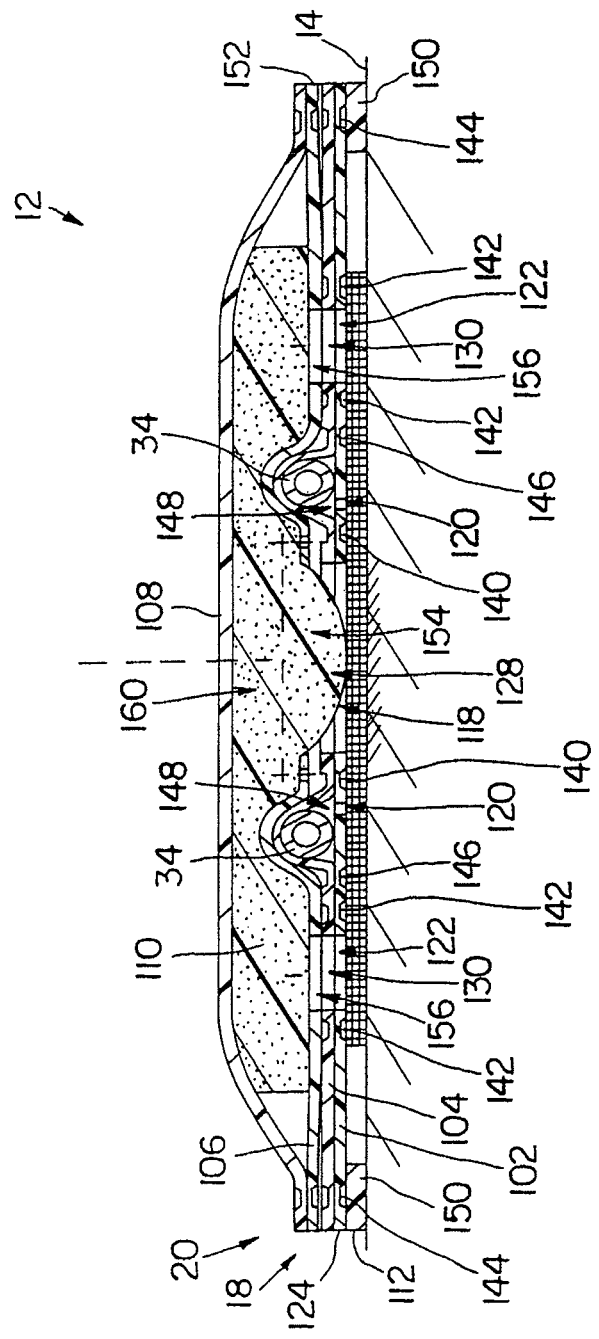
FIG. 9 is a sectional view taken along line 9-9 of FIG. 1.

Delivery bandage 18 further includes a sealing gasket 150 coupled to bottom sheet 102 adjacent its perimeter 112 as shown in FIGS. 4 and 9. Gasket 150 is illustratively a thin foam frame that includes an adhesive coating for coupling gasket 150 both to bottom sheet 102 and for removably coupling gasket 150 to a patient's skin 14. Gasket 150 provides an improved seal between bottom sheet 102 of delivery bandage 18 and skin 14 to allow wound treatment apparatus 10 to control the topical atmosphere adjacent wound 16. It is understood that other suitable materials can be used to provide a gasket, such as an appropriate layer of adhesive material.

Bottom sheet 106 of drainage bandage 20 includes a perimeter 152, central drainage passageway 154, and outer drainage passageways 156 that are configured to align with the corresponding perimeter 124 and passageways 128, 130 of top sheet 104 of delivery bandage 18. Bottom sheet 106 includes a thin layer of adhesive 158 formed as an open frame adjacent perimeter 152 to provide for removably coupling to delivery bandage top sheet 104. Adhesive 158 is configured to remain on bottom sheet 106 of drainage bandage 20 after uncoupling to allow for easy replacement of drainage bandage 20 without the need to remove delivery bandage 18.

Top sheet 108 of drainage bandage 20 has no passageways and is configured to align with bottom sheet 106 to provide a cavity 160 that receives adsorbent pad 110. Drainage bandage 20 is formed by sandwiching drainage tube 24 between top and bottom sheets 106, 108, which are then sealed together by RF welding adjacent their perimeters. Drainage bandage 20 thus channels wound effluent from delivery bandage 18, through pad 110, and out drainage tube 24 in an assembly that is easily replaceable, for example when adsorbent pad 110 becomes saturated or otherwise contaminated.

Bandage assembly 12 thus provides a two-piece bandage in which drainage bandage 20 can be removed and replaced while leaving delivery bandage 18 in situ. Drainage passageways 118, 122, 128, 130 thus allow for access to wound 16 through delivery bandage 18 when drainage bandage 20 is removed. Thus, a medical care giver can take a culture or sample from wound 16 without the need to remove delivery bandage 18.

Figure 11:
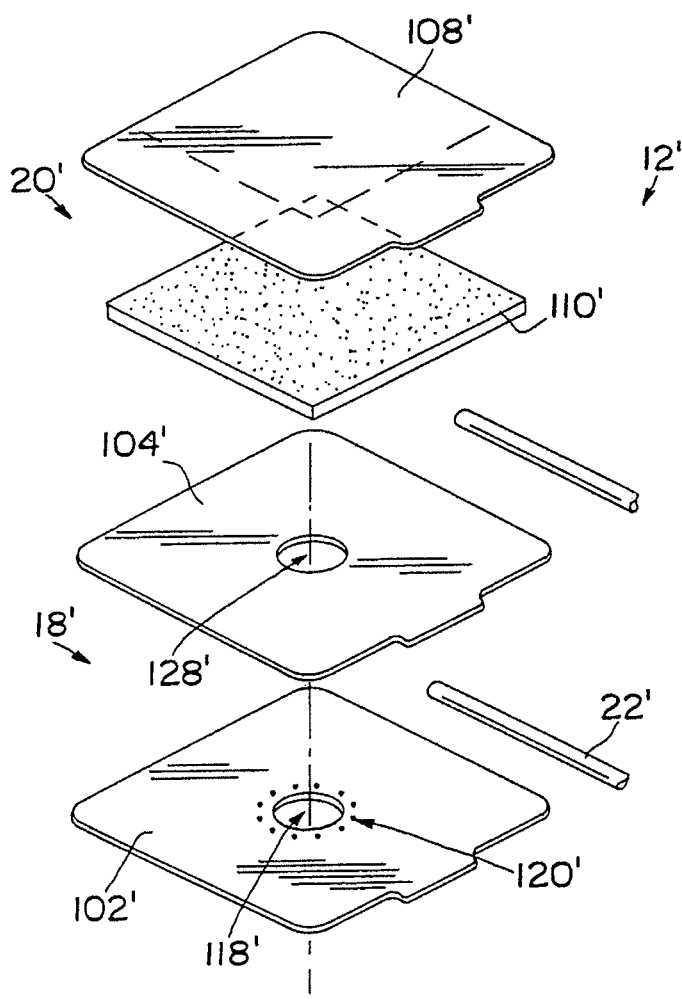
FIG. 11 is an exploded perspective view of an alternative embodiment of a bandage assembly.

An alternative embodiment bandage assembly 12' includes a one-piece combination delivery and drainage bandage comprising a delivery bandage portion 18' and drainage bandage portion 20' as shown in FIG. 11. Delivery bandage portion 18' includes a bottom sheet 102' that has a single drainage passageway 118' and a plurality of medicinal fluid delivery passageways 120'. Top sheet 104' includes a single drainage passageway 128'. Delivery bandage portion 18' includes a medicinal fluid supply tube 22' for use as discussed above in providing nebulized or liquid medication, etc. Drainage bandage portion 20' includes a pad 110', a top sheet 108', and a drainage tube 24'. Drainage tube 24' is coupled to bandage assembly 12' between sheets 104' and 108'.

Another alternative bandage assembly 12" is formed with only top and bottom sheets 102", 104" as shown in FIG. 12. Bottom sheet 102" includes a central drainage passageway 118" and a plurality of delivery passageways 120" arranged in a circular pattern radially outward of drainage passageway 118". A medicinal fluid supply tube 22" and a drainage tube 24" are coupled between top and bottom sheets 102", 104", with radio frequency welds (not shown) isolating the delivery tube and passageways 22", 120" from drainage tube 22" and passageway 118".

Yet another alternative bandage assembly 12'" is formed with elongated top and bottom sheets 102'", 104'" as shown in FIG. 13. Delivery passageways 118'" are arranged in a rectangular pattern to provide for delivery of fluid medication and control of the topical atmosphere adjacent a surface wound 16 having an elongated shape. Drainage passageway 120'" is illustratively circular, although drainage passageway 120'" can be formed in any suitable shape, such as an elongated rectangular or elliptical opening. Embodiment 12'" illustrates how bandages according to the present invention can readily be adapted for treatment of any wound shape by suitable geometric adaptations of the bandage assembly.

Figure 14:
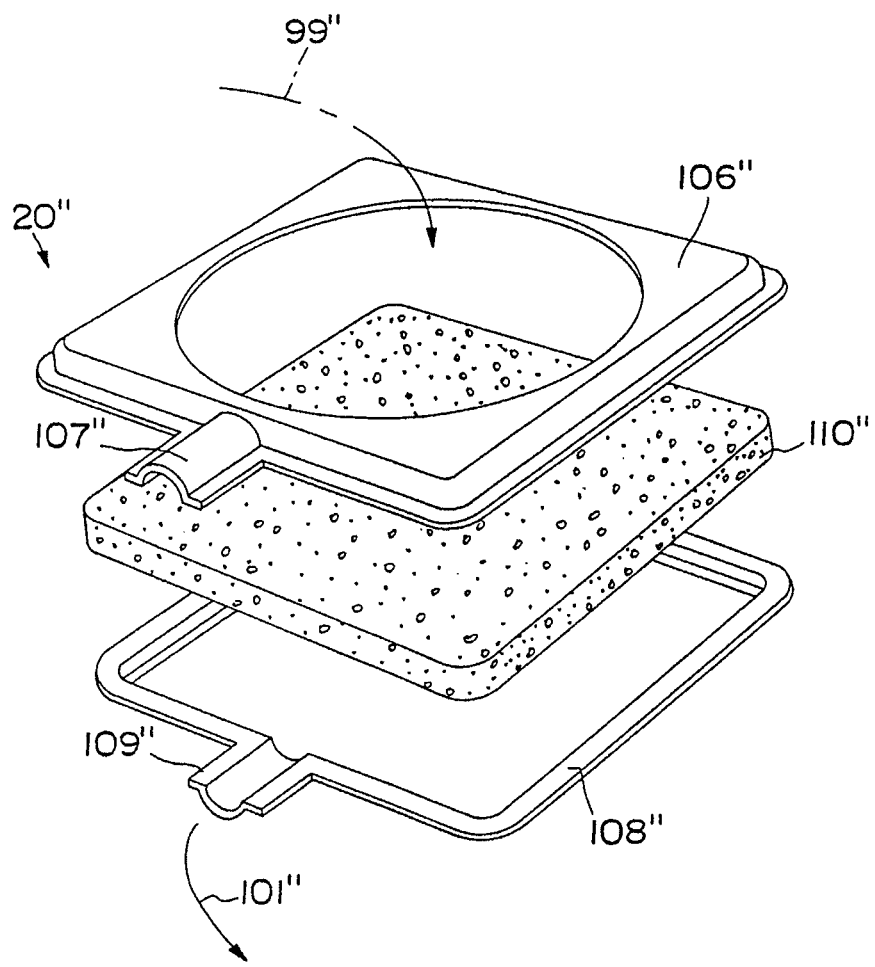
FIG. 14 is an exploded perspective view of an alternative embodiment of a drainage bandage.

Another alternative drainage bandage 20" includes a bottom sheet 106", a top sheet 108", and a pad 110" as shown in FIG. 14. Bottom and top sheets 106", 108" are formed with respective passageway portions 107", 109". Bandage 20" is formed by welding sheets 106", 108" together at their perimeters so that passageway portions 107", 109" form a passageway suitable for coupling to a drainage tube 24. Bandage 20" can be used as discussed above for bandage 20 so that wound effluent from a delivery bandage travels through drainage bandage 20" as shown by arrows 99", 101".

Figure 15:
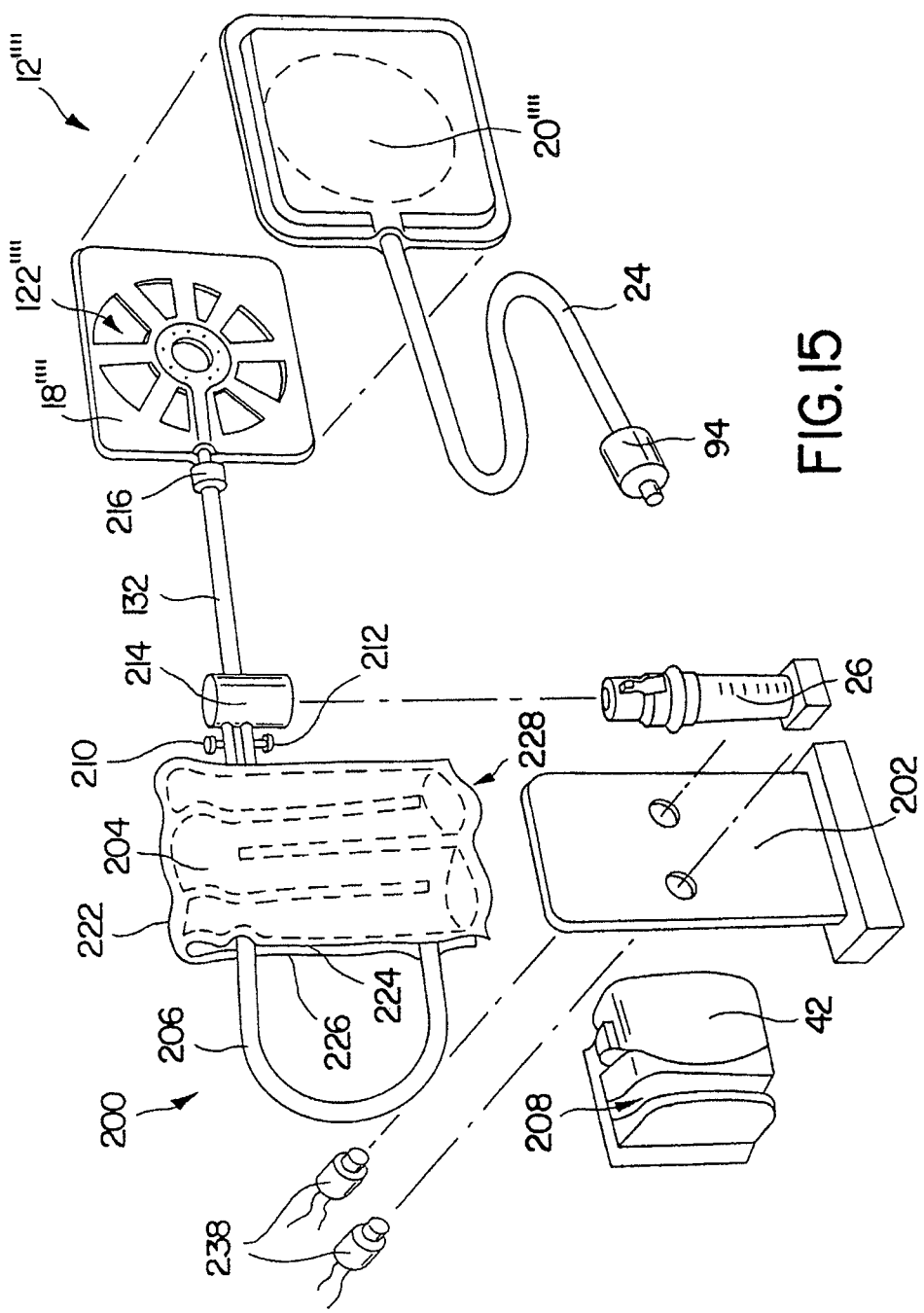
FIG. 15 is a diagrammatic perspective view of an alternative embodiment of a wound treatment apparatus.

As mentioned above, heater 40 can be replaced by other heating systems, such as recirculating fluid heating assembly 200 as shown in FIGS. 15-18. FIG. 15 also shows yet still another alternative embodiment bandage assembly 12"". Bandage assembly 12"" includes a delivery bandage portion 18"" that differs from delivery bandage 18 as shown in FIGS. 4-6 essentially in its outer wound drainage passageways 122"", which are formed as truncated arc segments. Bandage assembly 12"" includes a drainage bandage portion 20"" essentially the same as drainage bandage 20" discussed just above. Bandage assembly 12"" further includes a drainage tube 24 coupled to a wound drainage vapor filter 94.

Heating assembly 200 includes a radiant heating plate 202 configured to be coupled with a recirculating fluid path assembly 204 that transports recirculating fluid in a circuitous path past plate 202. As shown in FIG. 15, fluid path assembly 204 includes a tube section 206 configured to be laced into a channel 208 in a peristaltic pump 42 that pumps the recirculating fluid through assembly 200. Fluid path assembly 204 further includes input and output ports 210, 212 that are coupled to a nebulizer cap 214, which in turn is coupled both to a nebulizer 26 and to a multi-lumen tube 132 leading to bandage assembly 12"". Tube 132 is coupled to bandage assembly 12"" by a connector 216.

Figure 17:
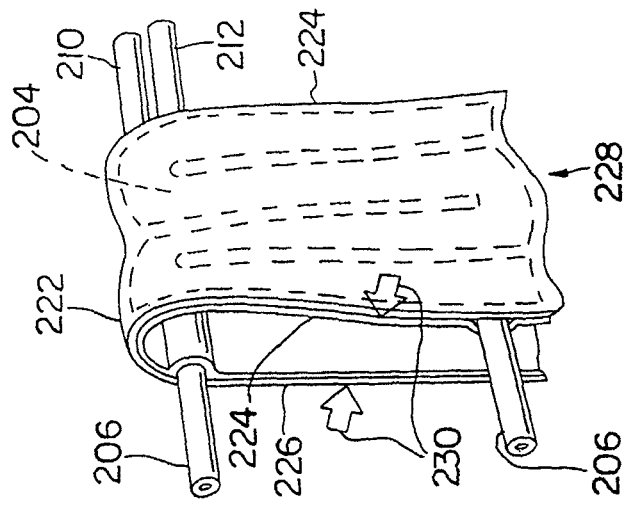
FIG. 17 is a perspective view of the fluid path assembly of FIG. 16.
Figure 16:
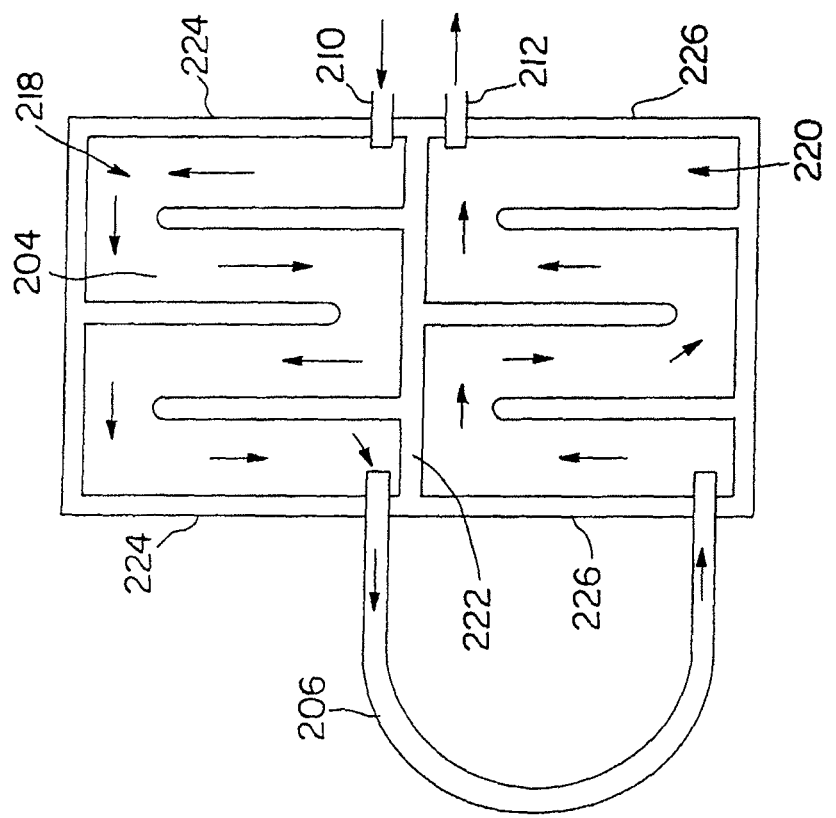
FIG. 16 is a plan view of a recirculating fluid path assembly from the heating assembly of FIG. 15.

Fluid path assembly 204 is illustratively formed by welding two flexible plastic sheets together to form a circuitous fluid input pathway 218 and a circuitous fluid output pathway 220 as shown in FIG. 16. Input pathway 218 is coupled to input port 210 and tube section 206; output pathway 220 is coupled to tube section 206 and output port 212. Fluid path assembly 204 is folded along its centerline 222 as shown in FIG. 17 so that input pathway 218 is opposite output pathway 220. Side edges 224, 226 that extend from centerline 222 are then welded together as shown by arrows 230 to create a pocket 228 configured to receive heating plate 202 so that recirculating fluid travels circuitously through fluid path assembly 204 past heating plate 202.

As fluid flows through fluid path assembly 204 past heating plate 202, fluid temperature is measured, for example, by infrared heat sensors 238. Recirculating fluid temperature is then regulated to a desired value by controlling the heat output of plate 202 selectively based on measured fluid temperature. It is understood that fluid path assembly 204 can be replaced by any suitable mechanism, such as a tube coupled to flexible sheets, or by forming narrow pathways or parallel pathways within flexible sheets, etc. Essentially, the requirement is to provide recirculating fluid pathways capable of receiving heat from plate 202 in order to regulate the temperature of fluid flowing through the pathways.

Figure 18:
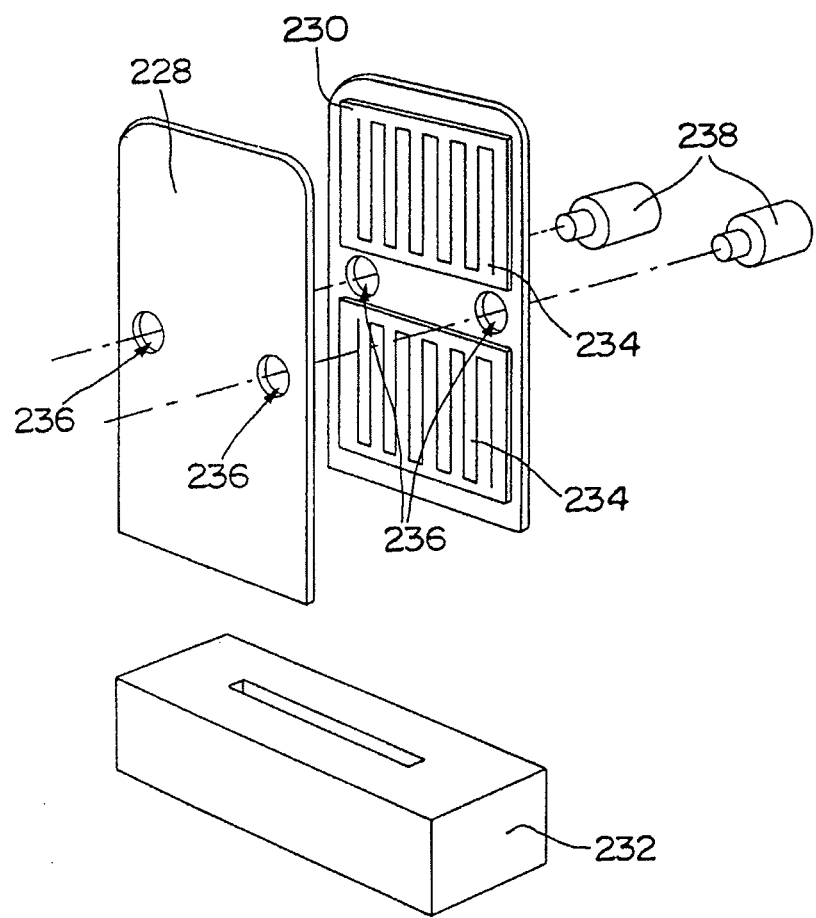
FIG. 18 is an exploded perspective view of the radiant heating plate of the heating assembly of FIG. 15.

Heating plate 202 is illustratively formed from two plate sections 228, 230 that are coupled to a base 232 as shown in FIG. 18. Plate sections 228, 230 include resistive heating elements 234 that are selectively controllable to heat recirculating fluid as it flows in fluid path assembly 204 past plate 202. Plate sections 228, 230 further include holes 236 to facilitate use of infrared temperature sensors for measuring recirculating fluid temperature. Plate 202 and sensors 238 are coupled to control system 44 to provide for automated temperature control of recirculating fluid.

Figure 19:
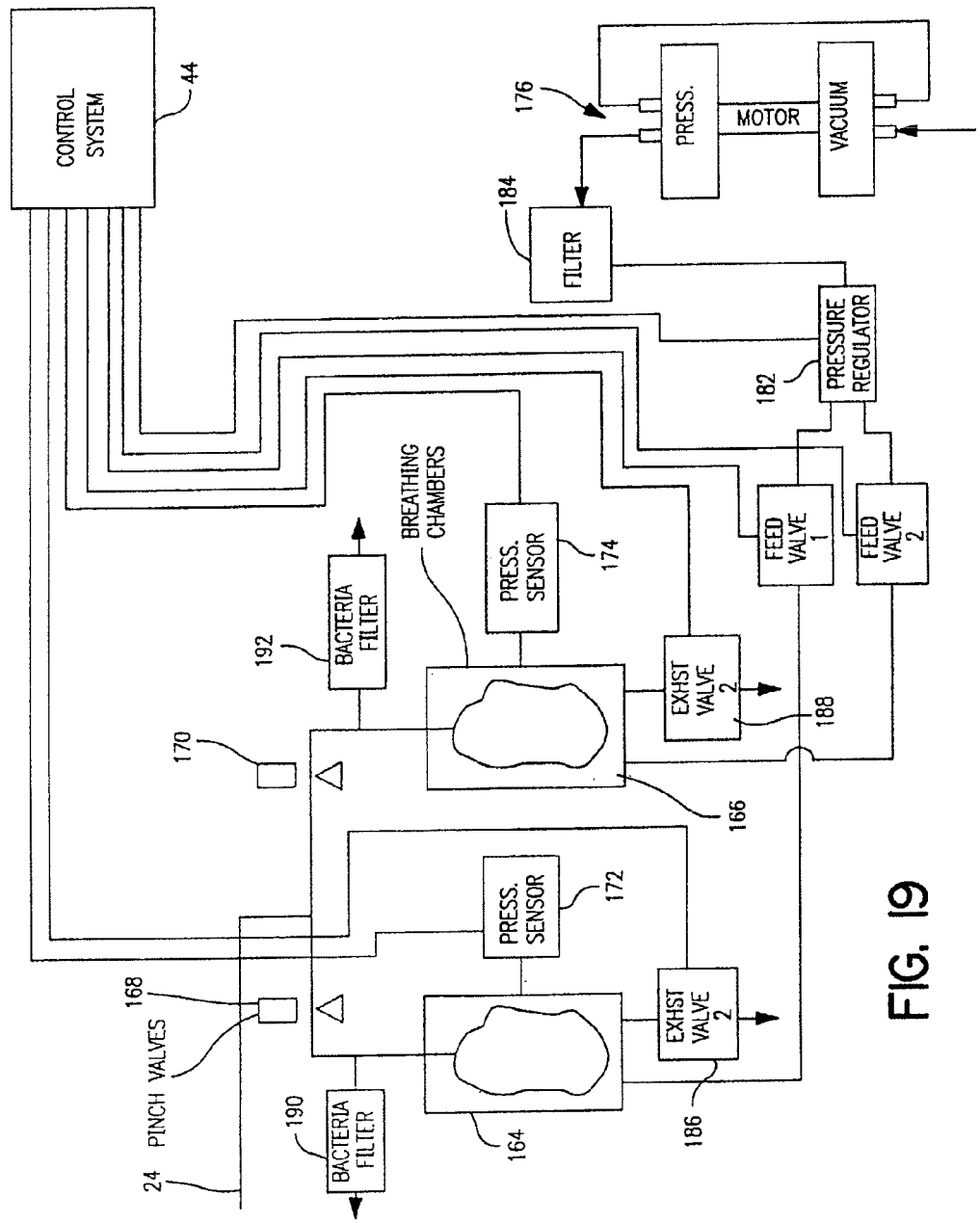
FIG. 19 is a system block diagram of an alternative drainage system embodiment.

An alternative drainage system 162 as shown in FIG. 19 can be used in the wound treatment apparatus 10, 10' of FIGS. 2 and 3 to provide for automated monitoring and switching of drainage bags by control system 44. Drainage system 162 includes first and second drainage bags 164, 166, and valves 168, 170 that are coupled between drainage bags 164, 166 and wound drainage tube 24. Drainage bags 164, 166 include pressure sensors 172, 174 that provide signals to control system 44 indicative of bag pressure, which correlates to whether the bag is full and needs to be changed. Bags 164, 166 further include bacteria filters 190, 192 and exhaust valves 186, 188 that control system 44 can use to vent excess pressure from within bags 164, 166.

Drainage bags 164, 166 are coupled to a pump 176 through valves 178, 180, pressure regulator 182, and filter 184. Valves 168, 170 are coupled to control system 44 to allow for automated selection of which drainage bag will receive effluent from bandage assembly 12, 12'. Drainage system 162 thus allows for automated and continuous operation of wound apparatus 10, 10'. In operation, valve 170 is closed and valve 168 is opened to permit filling of bag 164. When sensor 172 indicates to control system 44 that bag 164 is full, valve 168 is closed and valve 170 is opened to permit filling of bag 166. With valve 168 closed, valve 178 opens to supply pressure to bag 164 to force the contents of bag 164 out through bacteria filter 190. When sensor 174 detects that bag 166 is full, valve 170 is closed and valve 168 is opened to permit filling of bag 164 again. With valve 170 closed, valve 180 opens to supply pressure to bag 166 to force the contents of bag 166 out through bacteria filter 192. This cycle repeats itself so that tube 24 is not exposed to back pressure.

Referring now to FIGS. 20 and 21, an additional embodiment of wound treatment apparatus 320 comprises a medicinal fluid supply 322 to deliver fluid to wound 16, and a vacuum 326 and waste receptacle 324 to draw and store the fluid from wound 16. A supply tube 328 is connected to fluid supply 322 and to a fluid junction array 330. Fluid junction array 330 includes a fluid delivery conduit or deposit membrane 332 having an opening 333, and a circulating tube coupler 334. Opening 333 is positioned near wound 16. Illustratively, deposit membrane 332 can be made from two sheets laterally sealed on each side or it can be made from a simple tube. The material used to make membrane 332 can be rubber, plastic or any other suitable material. In addition, in one illustrative embodiment, membrane 332 has a flare 338 leading to opening 333, as best shown in FIG. 21. Flare 338 allows selective control over the flow rate of the medicinal fluid. The operator may cut membrane 332 thereby reducing its length, and increasing the flow of the medicine. The more flare 338 that is cut off, the faster the flow rate.

Circulating tube coupler 334 illustratively comprises dual ends 340 and 342, respectively. Each end illustratively 340 and 342 extend from opposite sides of membrane 332. (See FIG. 21.) Circulating tube 344 is connected to each end 340 and 342 encircling the periphery of wound 16 on healthy tissue. Fluid collection openings or notches 346 are formed intermittently along the length of tube 344. Illustratively, end 342 is connected to outlet tube 348 whereas end 340 is a terminated end. This forces all of the fluid in tube 344 to travel in one direction toward outlet tube 348. As a result, fluid flows out from membrane 332 passing over wound 16, drawing through notches 346 into tube 344, and exiting through outlet tube 348. Vacuum 326 communicates with outlet tube 348 via vacuum tube 350 and waste receptacle 324 to assist in drawing fluid from wound 16 into waste receptacle 324.

Circulating tube 344 may include a bendable wire 352 extending therethrough. Bendable wire 352 provides a semi-ridged form for tube 344 so that it may be selectively positioned about the periphery of wound 16 and hold its shape. As shown in FIG. 22, diameter 358 of bendable wire 352 is less than inner diameter 354 of circulating tube 344, thereby not inhibiting the flow of fluid.

Fluid junction array 330 attaches to adhesive 361 which adheres to a portion of healthy tissue surrounding wound 16. It is appreciated, however, that array 330 may be attached to the skin by any variety of suitable means. Top sheet 362 is sized to cover apparatus 320 and may be removably attached directly to healthy skin (not shown). Top sheet 362 is illustratively formed from a clear, flexible polyurethane or vinyl that meets USP Class VI requirements for medical applications. Gasket or border 360 is illustratively formed with a generally square perimeter having rounded corners attaching to the skin about the periphery of tube 344 and serves as a seal. In one embodiment, border 360 is positioned underneath top sheet 362, as shown in FIG. 21. In addition, border 360 attaches to array 330 by a pair of fasteners 364 that extend through apertures 366.

Figure 24:
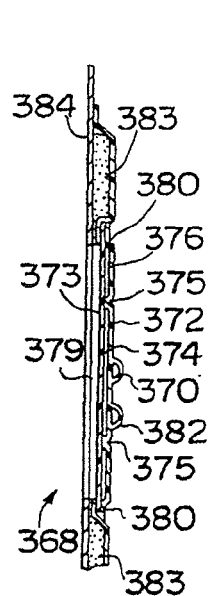
FIG. 24 is a sectional view of the wound treatment assembly from FIG. 23, taken along line B-B.
Figure 23:
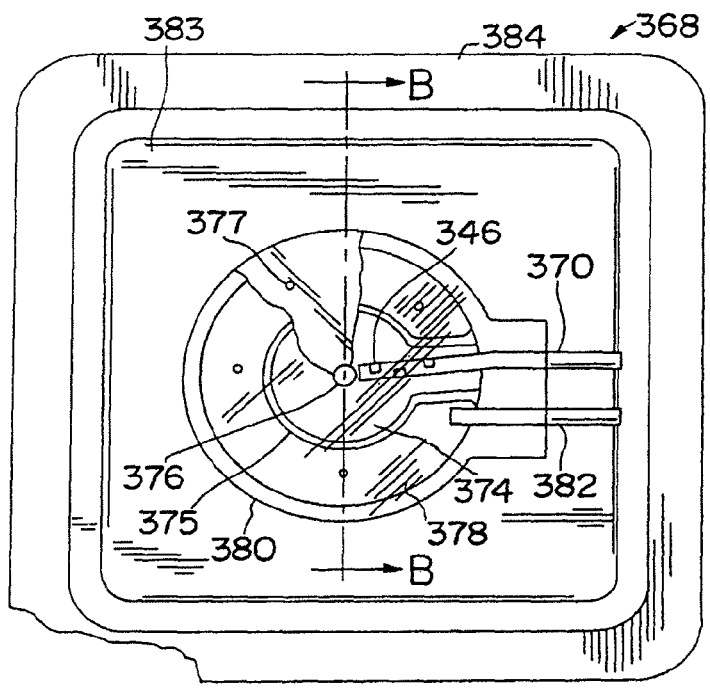
FIG. 23 is a top view of a wound treatment assembly including another embodiment of the present invention.

Another embodiment of the wound treatment apparatus is indicated by reference number 368 and is shown in FIGS. 23 and 24. A fluid supply tube 382 leads illustratively into outer chamber 378. Outer chamber 378 is formed about the periphery of inner chamber 374. Chambers 374 and 378 are formed by a top sheet and a bottom sheet 372 and 373, respectively. (See FIG. 24.) Illustratively, RF welds about the periphery of inner chamber 374 and about the periphery of outer chamber 378 further defines the chambers within sheets 372 and 373. The welds form an inner border and an outer border 375 and 380, respectively. It is understood that any suitable means can be used to form borders 375 and 380, in place of ultra-sonic welds. For example, borders 375 and 380 can be made from adhesive or from heat selectively applied to sheets 372 and 373.

A gasket 383 is attached about outer border 380 of the bandage. Gasket 383 suspends sheets 372 and 373 forming a wound cavity 379 as shown in FIG. 24. An adhesive 384 is attached to the underside of gasket 383 to adhere to healthy skin tissue surrounding the wound (not shown) thereby holding apparatus 368 in place and containing the medicinal fluid in wound cavity 379.

Illustratively, medicinal fluid is deposited through tube 382 into outer chamber 378. Several passageways 377 are disposed, in spaced relation to each other, through lower sheet 373 into wound cavity 379. Medicinal fluid can then flow through passageways 377 into wound cavity 379 and onto the wound. The fluid is then drawn from the surface of the wound up through outlet aperture 376. Outlet aperture 376 is disposed through lower sheet 373 into inner chamber 374. With the assistance of a vacuum connected to outlet tube 370, the medicinal fluid is drawn from inner chamber 374 into tube 370 and ultimately into a waste receptacle. Fluid collection openings or notches 346 are formed intermittently along the length of tube 370 within inner chamber 374 to further assist in collecting fluid.

It is appreciated that the flow direction of the medicinal fluid may be reversed from that previously described. Illustratively, medicinal fluid can enter apparatus 368 through outlet tube 370, and dispense through aperture 376 into wound cavity 379. Fluid can then be drawn through apertures 377 into outer chamber 378 and out through tube 382. Apertures 377 may be of any size suitable to draw the fluid from wound cavity 379 into chamber 378.

Figure 26:
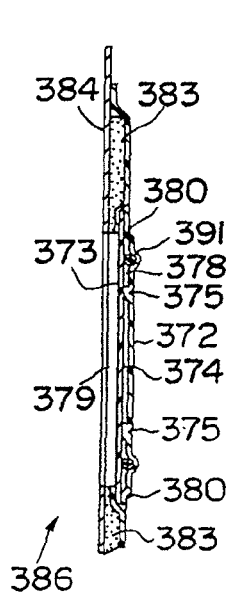
FIG. 26 is a sectional view of the wound treatment assembly from FIG. 25, taken along line C-C.
Figure 25:
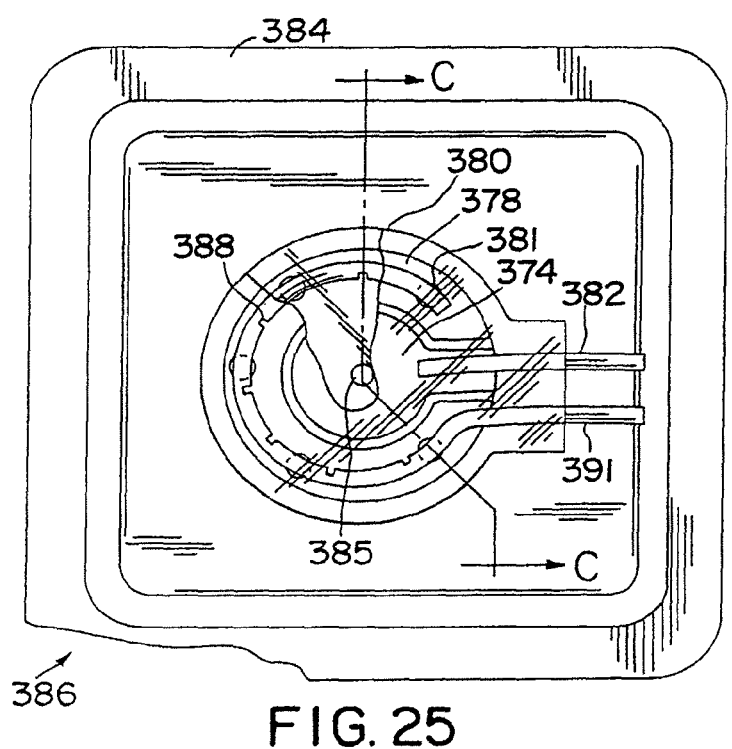
FIG. 25 is a top view of a wound treatment assembly in accordance with a still further embodiment of the present invention.

A still further embodiment of the wound treatment apparatus is indicated by reference number 386 and is shown in FIGS. 25 and 26. In contrast to the previous embodiment, fluid supply tube 382 leads illustratively into inner chamber 374. Like the previous embodiment, outer chamber 378 is formed about the periphery of inner chamber 374. In addition, chambers 374 and 378 are formed by a top sheet and a bottom sheet 372 and 373, respectively. (See FIG. 26.) Again, illustratively, an RF weld about the periphery of inner chamber 374 and at the periphery outer chamber 378 further defines the chambers within sheets 372 and 373. The welds form an inner border and an outer border 375 and 380, respectively. It is understood that any suitable means can be used to form borders 375 and 380, in place of RF welds.

Illustratively, medicinal fluid is deposited through tube 382 into inner chamber 374. This is in contrast to the previous embodiment where tube 382 deposited fluid into outer chamber 378. Medicinal fluid can then flow through inlet aperture 385 that is disposed through bottom sheet 373 into wound cavity 379 and onto the wound. Several passageways 381 are disposed, in spaced relation to each other, through lower sheet 373 into wound cavity 379. In one illustrative embodiment, passageways 381 are larger in size than passageways 377 in the previous embodiment. The fluid is drawn from the surface of the wound up through passageways 381. In one embodiment, openings or notches 346 are formed intermittently along the portion of tube 391 extended within outer chamber 378. Tube 391 illustratively extends through outer chamber 380. With the assistance of a vacuum connected to outlet tube 391, the medicinal fluid is drawn up from outer chamber 378 into tube 391 and ultimately into a waste receptacle. Other features like gasket 383 and adhesive 384 are configured similar to that of the previous embodiment.

It is appreciated that the flow direction of the medicinal fluid may be reversed from that previously described. Illustratively, medicinal fluid can enter apparatus 386 through tube 391, flow out notches 388 and dispense through apertures 381 into wound cavity 379. Fluid can then be drawn through aperture 385 into inner chamber 374 and out through tube 382. Apertures 381 may be of any size suitable to dispense the fluid from outer chamber 378 into wound cavity 379.

Figure 27:
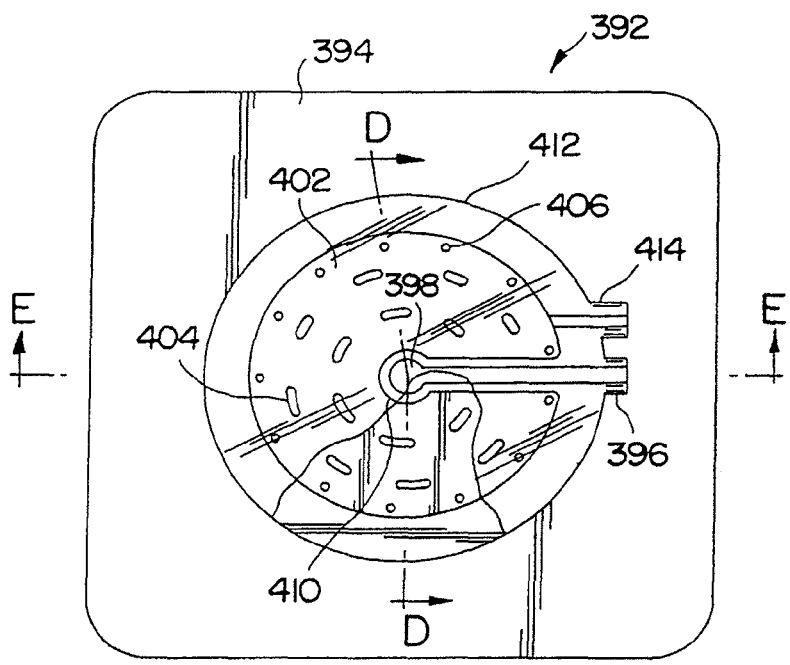
FIG. 27 is a top view of a wound treatment assembly in accordance with an additional embodiment of the present invention.
Figure 28:
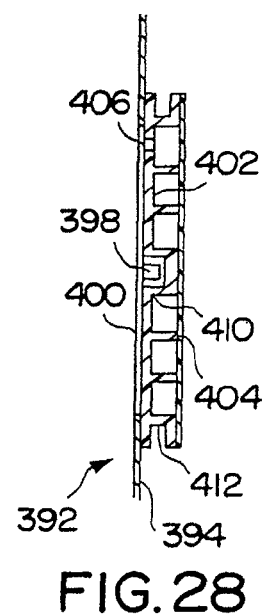
FIG. 28 is a sectional view of the wound treatment assembly from FIG. 27, taken along line D-D.
Figure 29:
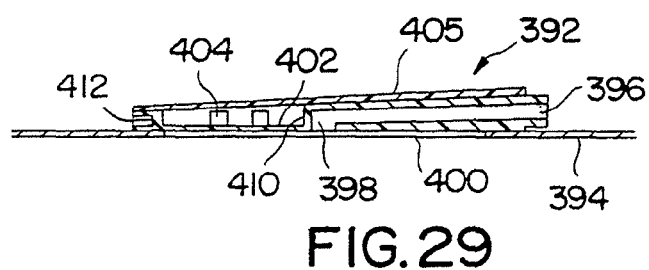
FIG. 29 is a sectional view of the wound treatment assembly from FIG. 27, taken along line E-E.

An additional embodiment of a wound treatment apparatus is indicated by reference number 392 and is shown in FIGS. 27-29. Wound apparatus 392 comprises a fluid supply tube 396 extending illustratively near the center of apparatus 392 into a dispensing aperture 398. Aperture 398 opens to a wound cavity 400 formed on the underside of apparatus 392. (See FIGS. 28 and 29.) Above wound cavity 400 and formed about dispensing aperture 398 is basin 402. Basin 402 is defined by inner and outer walls 410 and 412, respectively. Inner wall 410 separates the basin 402 from dispensing aperture 398. Outer wall 412 illustratively defines the periphery of basin 402. Columns 404 extend from basin 402, illustratively in a circular formation about inner wall 410, as shown in FIG. 27. A top sheet 405 is formed over basin 402, attaching illustratively to the top of outer wall 412. Columns 404 support top sheet 405 over basin 402. Top sheet 405 is thereby prevented from collapsing in on basin 402 and covering passageways 406 as a negative pressure is applied to bandage 392.

An adhesive 394 is attached to apparatus 392 illustratively about the periphery of cavity 400. As with previous embodiments, adhesive 394 adheres to healthy skin tissue surrounding the wound. It is appreciated that adhesive 394 may be replaced with any variety of means to secure wound apparatus 392 over the wound.

Illustratively, medicinal fluid flows from tube 396 through aperture 398 into wound cavity 400 and onto the wound. The fluid then draws up through passageways 406 collecting in basin 402. The collected fluid is then drawn from basin 402 into outlet tube 414 and ultimately into a waste receptacle (not shown). As with other embodiments previously discussed, a vacuum may illustratively be attached to outlet tube 414 in the manner previously described.

It is appreciated, however, that the flow direction of the medicinal fluid in apparatus 392 may be reversed from that previously described. Illustratively, medicinal fluid can enter through tube 414, flow into wound cavity 400 through passageways 406. The fluid can then be drawn through aperture 398 into tube 396. Apertures 406 may be of any size suitable to dispense or draw the fluid to or from wound cavity 400.

Figure 30:
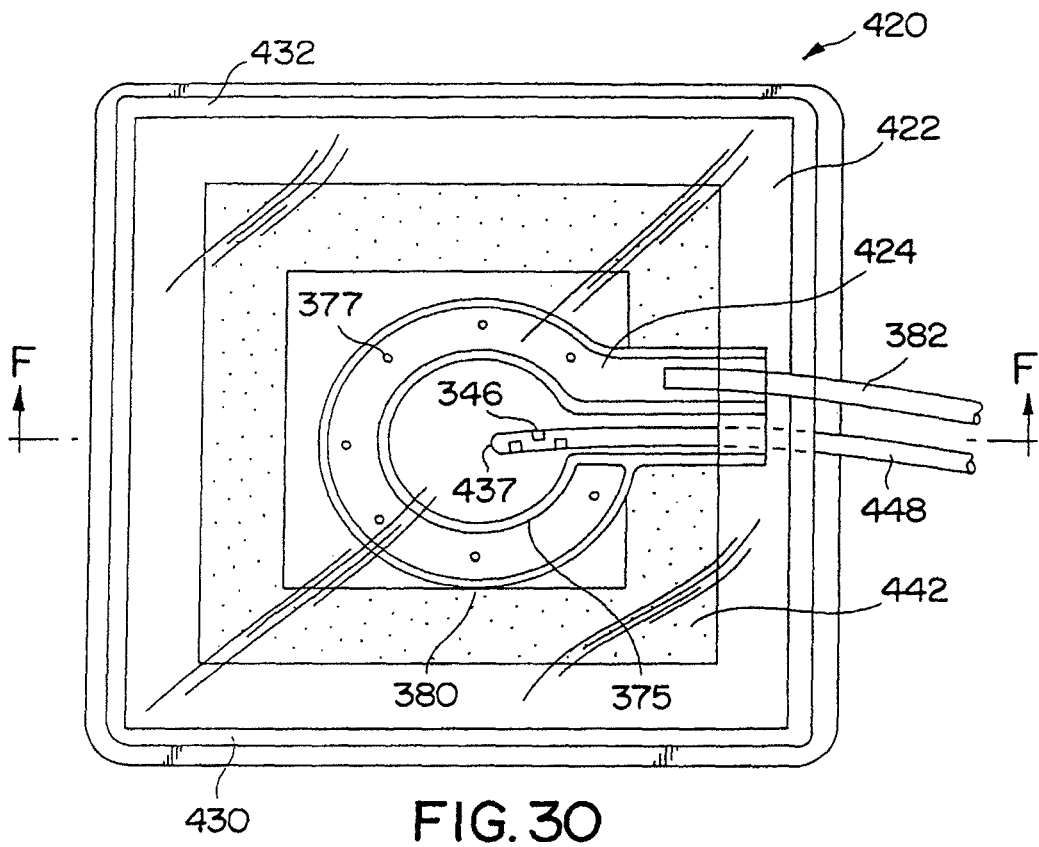
FIG. 30 is a top view of a flexible wound treatment assembly in accordance with the present invention.
Figure 31:
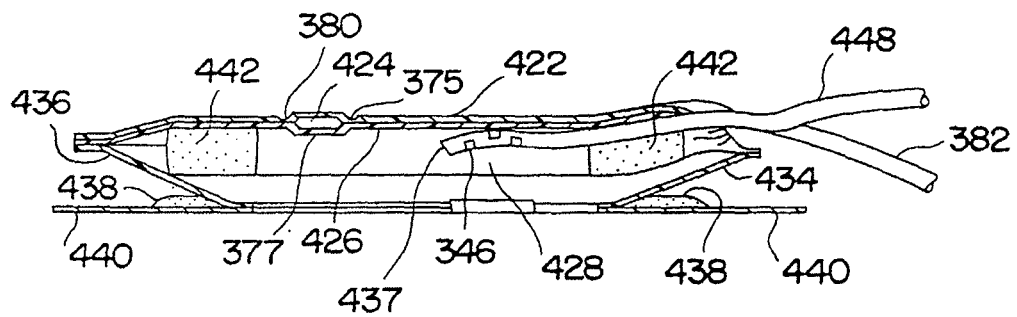
FIG. 31 is a sectional view of the flexible wound treatment assembly from FIG. 30, taken along line F-F.
Figure 32:
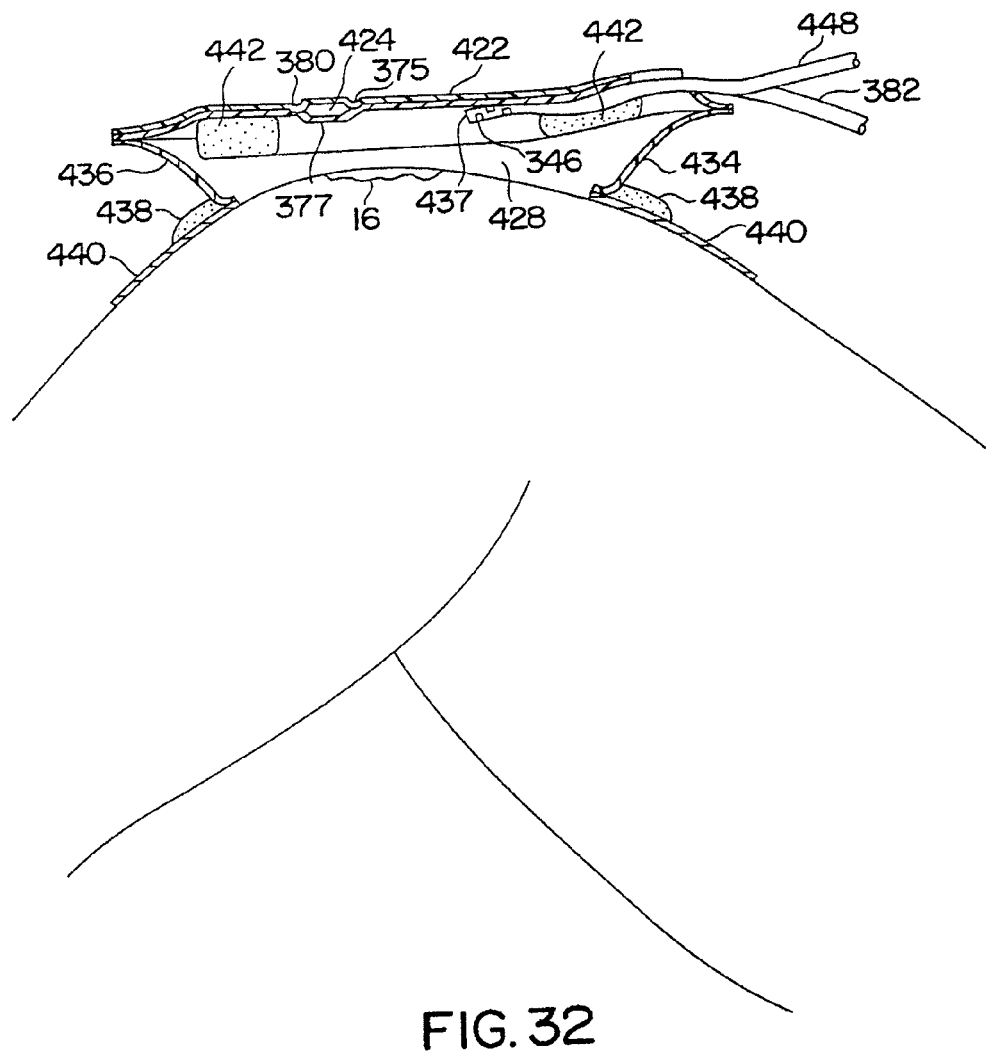
FIG. 32 is a sectional view of the flexible wound treatment assembly from FIG. 31, applied over a wound on a bendable joint.

Another embodiment of the present invention includes a flexible wound treatment apparatus 420 shown in FIGS. 30-32. An inlet tube 382 is extended through top panel 422 into chamber 424. Chamber 424 is formed between top panel 422, mid-panel 426, and is defined by inner and outer borders 375 and 380, respectively. (See FIGS. 30 and 31.) Illustratively, an RF weld about the peripheries of chamber 424 forms borders 375 and 380 as previously discussed. Several apertures 377 are disposed through mid-panel 426 into an expanded wound cavity 428. Wound cavity 428 is defined by two laterally spaced side walls 430 and 432 and two end walls 434 and 436 extending between said side walls 430 and 432. Mid-panel 426 interconnects to the coplanar edges of walls 430, 432, 434, and 436. The resultant form is a flexible bellow or flexible body. A spacer 442 is fitted within the periphery of wound cavity 440. Spacer 442 is illustratively made from a foam material but it is understood that it can be made from any suitable material that will assist in maintaining the form of the expanded wound cavity 428 as shown in FIGS. 31 and 32.

Formed about the periphery of wound cavity 428 and attached to coplanar edges of said walls 430, 432, 434, and 436 opposite mid panel 426, is a pad 438. Pad 438 is illustratively made from a thin flexible foam material and often with a plastic-like top coating. Pad 438 provides a cushioning intermediary between the walls 430, 432, 434, and 436, and an adhesive 440. Adhesive 440, is a similar panel to those adhesives described in the previous embodiments.

Flexible wound treatment apparatus 420 is optimum for use on flexible joints like knees and elbows. This is because spacer 442 keeps mid-panel 426 raised enough so that as wound 16 is raised as the joint bends, wound 16 will not be interfered with by mid-panel 426. (See FIG. 32.)

Illustratively, and in similar fashion to previous embodiments, tube 382 deposits medicinal fluid into chamber 424 where it flows through passageways 377 into cavity 428. An outlet tube 448 is extended illustratively through top panel 422, over spacer 442, and into wound cavity 428. Notches 346 can be formed in the length of tube 448 positioned within cavity 428 so that after the fluid has deposited onto wound 16 it is drawn up through opening 437 and/or notch 346 into outlet tube 448. Like previous embodiments, it is understood that the flow of the medicinal fluid can be reversed. The fluid can be deposited onto wound 16 by tube 448 and drawn up through passageways 377 into chamber 424 and out tube 382.

Figure 33:
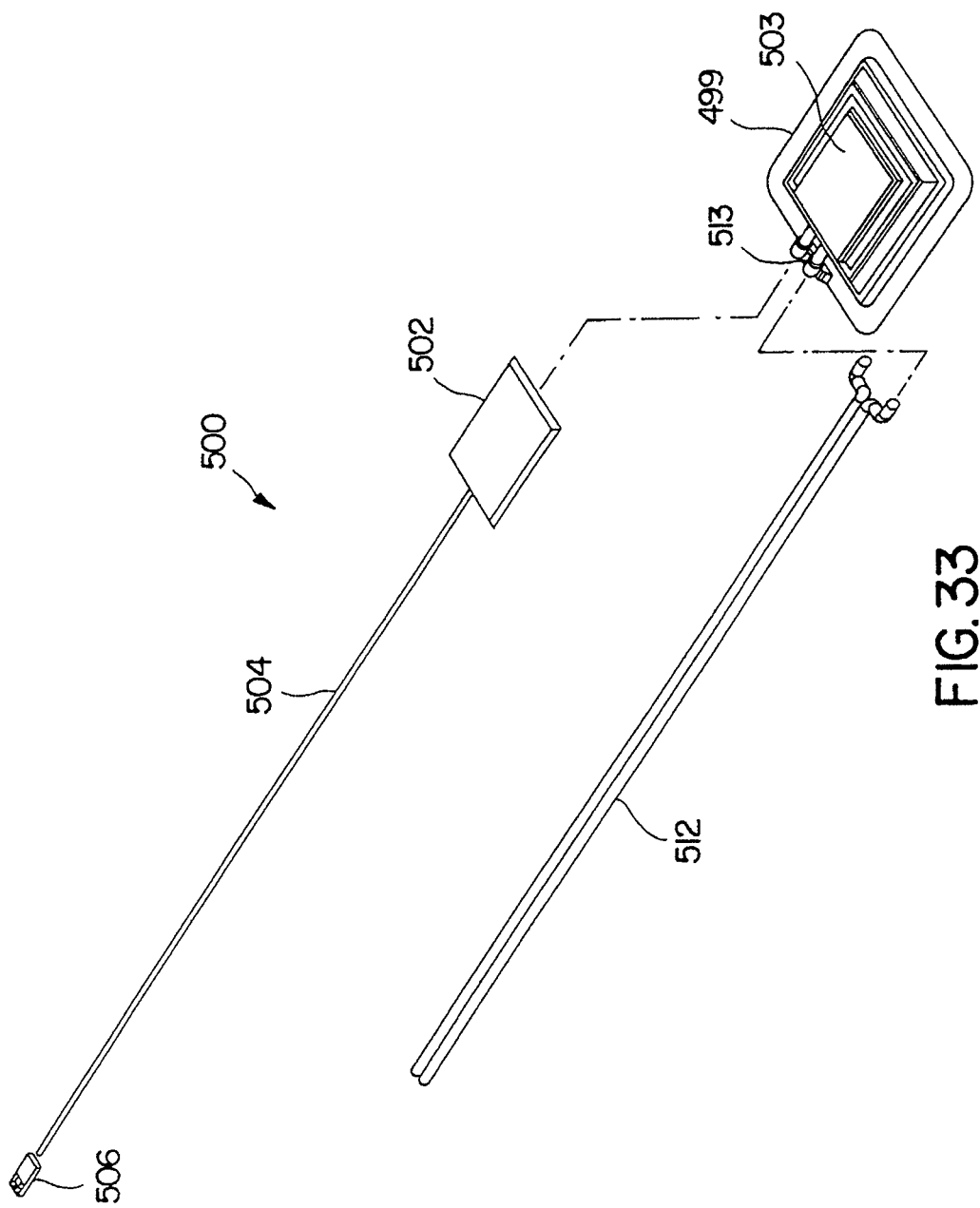
FIG. 33 is a perspective view of a wound treatment apparatus including a heating system.
Figure 34:
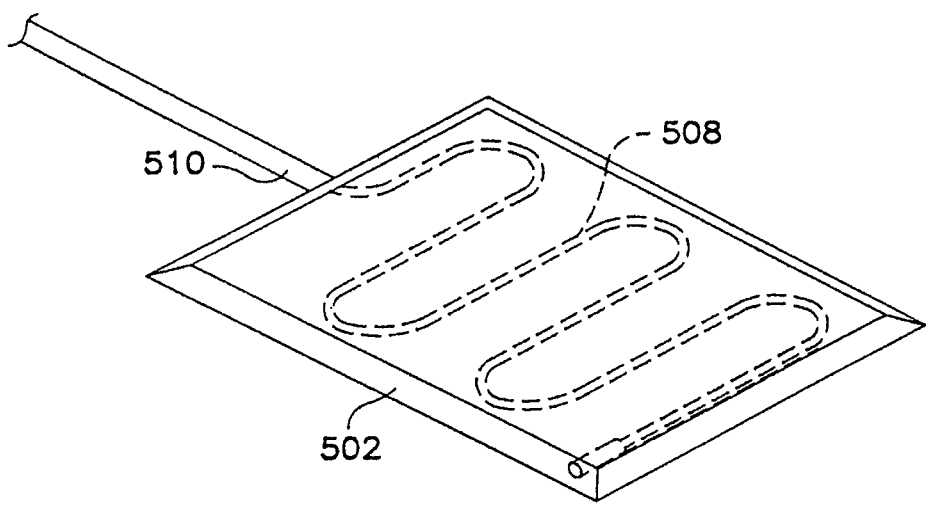
FIG. 34 is a perspective clear view of a portion of the wound treatment apparatus from FIG. 33.

A further embodiment of the present invention comprises a heat and heat sensing system 500 (collectively, heat system 500) coupled, illustratively, with bandage 499 as shown in FIG. 33. It is appreciated that heat system 500 can be coupled with any bandage described herein. Heat system 500 includes a heating and sensing pad 502, thermocouples 508 and 510, a tube assembly 504, and a patch unit connector 506. Pad 502 is the portion of system 500 that transfers heat to bandage 499 as well as senses the amount of heat that was transferred. Illustratively, pad 502 includes a thermocouple 508 that supplies heat to pad 502, See FIG. 34. A second thermocouple 510 senses the heat that is being supplied by thermocouple 508. Pad 502 can be made, illustratively from silicone, but it is appreciated that pad 502 can be made from any suitable material serving the same function as silicone. Pad 502 can be either inserted into a pocket 503 within the bandage or coupled to the bandage by any suitable means. In addition, alternatives to pad 502 can be used to transfer heat from thermocouple 508 to bandage 499. Both thermocouples 508 and 510 extend from pad 502 to patch unit connector 506. Illustratively, the thermocouples can be contained in tube 504 protecting same. Tube 504 can be flexible and made from any suitable material, and be of any suitable length.

Patch connector 506 connects to a nebulizer cartridge (not shown) and can be removed for continual use on additional bandages. A double lumen tube 512 can connect to tube connector 513 to supply medicinal fluid to bandage 499 and draw fluid away from same, as hereinbefore described.

Although the invention has been described in detail with reference to certain preferred embodiments, variations and modifications exist within the scope and spirit of the present invention as described and defined in the following claims.

The invention claimed is:

1. A wound treatment apparatus comprising:
    a fluid drainage tube configured to be coupled to a fluid drainage passageway of a wound bandage;
    first and second fluid drainage receptacles coupled to the drainage tube;
    first and second inlet valves coupled between the fluid drainage tube and the first and second fluid drainage receptacles, respectively; and
    first and second outlet valves coupled to the first and second fluid drainage receptacles, respectively, on one side of each outlet valve and configured to be coupled to a vacuum source for providing a negative pressure on the other side of each outlet valve;
    wherein the first inlet valve and the first outlet valve are configured to be opened to fill the first fluid drainage receptacle and the second inlet valve is closed to prevent the second fluid drainage receptacle from filling.

2. The apparatus of claim 1, further comprising a vacuum source coupled to the first and second outlet valves such that the vacuum source can communicate negative pressure to the first and second fluid drainage receptacles.

3. The apparatus of claim 2, further comprising a bandage including a wound facing surface configured to face toward a wound and a fluid drainage passageway having an opening adjacent the wound facing surface, the fluid drainage passageway configured to be coupled to the fluid drainage tube.

4. The apparatus of claim 2, further comprising a controller coupled to the first and second inlet valves, the controller configured to select which fluid drainage receptacle can receive fluid from fluid drainage tube.

5. The apparatus of claim 4, wherein the valves are pinch valves.

6. The apparatus of claim 4, further comprising a first sensor coupled to the first fluid drainage receptacle to provide a signal indicative of an amount of fluid in the first fluid drainage receptacle.

7. The apparatus of claim 6, further comprising a second sensor coupled to the second drainage receptacle to provide a signal indicative of an amount of fluid in the second fluid drainage receptacle.

8. The apparatus of claim 7, where the first and second sensors are pressure sensors.

9. The apparatus of claim 7, further comprising a first exhaust valve coupled to the first fluid drainage receptacle such that the first exhaust valve can be opened to vent excess pressure from the first fluid drainage receptacle, and a second exhaust valve coupled to the second fluid drainage receptacle such that the second exhaust valve can be opened to vent excess pressure from the second fluid drainage receptacle.

10. The apparatus of claim 9, where the first and second exhaust valves are coupled to the controller such that the controller can open the exhaust valves.

11. The apparatus of claim 1, wherein the second inlet valve and the second outlet valve are configured to be opened to fill the second fluid drainage receptacle and the first inlet valve is closed to prevent the first fluid drainage receptacle from filling.

12. A wound treatment apparatus comprising:
    a fluid drainage tube coupled to a fluid drainage passageway of a wound bandage, the fluid drainage tube configured to be coupled to a bandage including a wound facing surface configured to face toward a wound, the fluid drainage passageway having an opening adjacent the wound facing surface;
    first and second fluid drainage receptacles coupled to the drainage tube;
    first and second valves coupled between the fluid drainage tube and the first and second fluid drainage receptacles, respectively;
    a vacuum source coupled to the first and second fluid drainage receptacles such that the vacuum source can communicate negative pressure:
        through the first fluid drainage receptacle to the drainage tube if the first valve is open; and through the second fluid drainage receptacle to the drainage tube if the second valve is open; and
    a controller coupled to the first and second valves, the controller configured to:
        permit the first fluid drainage receptacle to receive fluid from the fluid drainage tube while preventing the second fluid drainage receptacle from receiving fluid from the fluid drainage tube, until the first fluid drainage receptacle reaches a fill threshold; and
        upon the first fluid drainage receptacle reaching the fill threshold, permit the second fluid drainage receptacle to receive fluid from the fluid drainage tube while preventing the first fluid drainage receptacle from receiving fluid from the fluid drainage tube.

13. The apparatus of claim 12, wherein the valves are pinch valves.

14. The apparatus of claim 12, further comprising a first sensor coupled to the first fluid drainage receptacle to provide a signal indicative of an amount of fluid in the first fluid drainage receptacle.

15. The apparatus of claim 14, further comprising a second sensor coupled to the second drainage receptacle to provide a signal indicative of an amount of fluid in the second fluid drainage receptacle.

16. The apparatus of claim 15, where the first and second sensors are pressure sensors.

17. The apparatus of claim 15, further comprising a first exhaust valve coupled to the first fluid drainage receptacle such that the first exhaust valve can be opened to vent excess pressure from the first fluid drainage receptacle, and a second exhaust valve coupled to the second fluid drainage receptacle such that the second exhaust valve can be opened to vent excess pressure from the second fluid drainage receptacle.

18. The apparatus of claim 17, where the first and second exhaust valves are coupled to the controller such that the controller can open the exhaust valves.

* * * * *